US012702389B2

(12) United States Patent
Addison et al.

(10) Patent No.: US 12,702,389 B2
(45) Date of Patent: Aug. 11, 2026

(54) BIOPSY SYSTEM AND BIOPSY DRIVER USE FOR THEREWITH

(71) Applicant: Bard Peripheral Vascular, Inc., Franklin Lakes, NJ (US)

(72) Inventors: Jordan Addison, Gilbert, AZ (US); Amy Bui, Chandler, AZ (US); Bryon Pelzek, Gold Canyon, AZ (US); Ranjani Sampath Kumaran, Tempe, AZ (US); Ryan Striedel, Tempe, AZ (US)

(73) Assignee: Bard Peripheral Vascular, Inc., Franklin Lakes, NJ (US)

( * ) Notice: Subject to any disclaimer, the term of this patent is extended or adjusted under 35 U.S.C. 154(b) by 392 days.

(21) Appl. No.: 18/556,929

(22) PCT Filed: Apr. 30, 2021

(86) PCT No.: PCT/US2021/030080

§ 371 (c)(1),
(2) Date: Oct. 24, 2023

(87) PCT Pub. No.: WO2022/231610

PCT Pub. Date: Nov. 3, 2022

(65) Prior Publication Data

US 2024/0206860 A1 Jun. 27, 2024

(51) Int. Cl.
*B01F 35/221* (2022.01)
*A61B 10/02* (2006.01)
(Continued)

(52) U.S. Cl.
CPC ........ *A61B 10/025* (2013.01); *A61B 17/1637* (2013.01); *A61B 2017/00115* (2013.01);
(Continued)

(58) Field of Classification Search
CPC .............. A61B 10/025; A61B 17/1637; A61B 2017/00115; H01H 9/063; B01F 35/22161
See application file for complete search history.

(56) References Cited

U.S. PATENT DOCUMENTS

2007/0085496 A1* 4/2007 Philipp ............ B01F 35/22161 318/139
2008/0105243 A1* 5/2008 Monks .................... F41B 11/71 124/31

(Continued)

FOREIGN PATENT DOCUMENTS

| | | | |
|---|---|---|---|
| EP | 1870044 | A1 | 12/2007 |
| JP | 2003211371 | A | 7/2003 |
| JP | 2017087412 | A | 5/2017 |

OTHER PUBLICATIONS

International Search Report and Written Opinion for Appln. No. PCT/US2021/030080, mailed Mar. 10, 2022, 13 pages.

(Continued)

*Primary Examiner* — Cortez M Cook
(74) *Attorney, Agent, or Firm* — Dinsmore & Shohl LLP

(57) ABSTRACT

A biopsy driver includes a housing, a battery supply, a motor, a trigger, and a control circuit. The control circuit has a trigger switch circuit, a resistance network circuit, and a pulse width modulation circuit. The trigger switch circuit has an OFF state and an ON state. The resistance network circuit is coupled to an input of the pulse width modulation circuit. The pulse width modulation circuit is configured to generate a variable pulse width signal to control a rotational speed of the motor. When the trigger switch circuit is in the ON state, the trigger switch circuit is configured to: connect a negative terminal of the battery supply to the chassis ground, and select a resistance value from the resistance network circuit to select a desired duty cycle of the variable (Continued)

pulse width signal generated by the pulse width modulation circuit.

25 Claims, 8 Drawing Sheets

(51) Int. Cl.
*A61B 17/16* (2006.01)
*A61B 17/00* (2006.01)

(52) U.S. Cl.
CPC ............... *A61B 2017/00398* (2013.01); *A61B 2017/00734* (2013.01)

(56) References Cited

U.S. PATENT DOCUMENTS

2018/0082804 A1 3/2018 Fangmann
2020/0129186 A1 4/2020 Miller et al.
2020/0235638 A1* 7/2020 Velderman ............. H01H 9/063

OTHER PUBLICATIONS

Japanese Office Action for Appl. No. 2023-125296, mailed Dec. 16, 2024, 21 pages.

* cited by examiner

BIOPSY SYSTEM AND BIOPSY DRIVER USE FOR THEREWITH

CROSS-REFERENCE TO RELATED APPLICATIONS

The present application is a U.S. National Phase of and claims priority to International Application No. PCT/US2021/030080, entitled "Biopsy System & Biopsy Driver Use for Therewith" and filed Apr. 30, 2021, which is incorporated herein by reference in its entirety.

TECHNICAL FIELD

The present invention relates to a biopsy driver, and a biopsy apparatus, and, more particularly, to a biopsy system and biopsy driver for use therewith.

BACKGROUND ART

A bone biopsy surgical procedure involves the use of surgical devices for providing access to bone tissue, e.g., the cortical bone or bone marrow, of a patient. Such surgical devices may include a handheld motorized drill that may utilize an electric or pneumatic motor to rotate a cutting element of an intraosseous device, such as a biopsy needle. In some applications, the biopsy needle is to releasably connect the driveshaft of the motorized drill so as to facilitate a substitution of the biopsy needle during the bone biopsy procedure.

SUMMARY OF INVENTION

The invention, in one form, is directed to a biopsy driver that includes a housing, a battery supply, a motor, a trigger, and a control circuit. The battery supply is contained in the housing. The battery supply has a positive terminal and a negative terminal. The negative terminal is selectively coupled to or decoupled from a chassis ground, e.g., by the control circuit. The motor is contained in the housing. The motor has a driveshaft. The motor has a first power input terminal and a second power input terminal. A trigger is coupled to the housing and accessible external to the housing. The control circuit is mounted to the housing and is electrically coupled to the motor. The control circuit has a trigger switch circuit, a resistance network circuit, and a pulse width modulation circuit. The trigger switch circuit has an OFF state and an ON state. The resistance network circuit is coupled to an input of the pulse width modulation circuit. The pulse width modulation circuit is configured to generate a variable pulse width signal to control a rotational speed of the motor. When the trigger switch circuit is in the ON state, the trigger switch circuit is configured to: connect the negative terminal of the battery supply to the chassis ground; and select a resistance value from the resistance network circuit to select a desired duty cycle of the variable pulse width signal generated by the pulse width modulation circuit.

The invention, in another form, is directed to a biopsy driver that includes a housing, a battery supply, a motor, a trigger, and a control circuit. The battery supply is contained in the housing. The battery supply has a positive terminal and a negative terminal. The negative terminal is selectively coupled to a chassis ground, e.g., by the control circuit. The motor is contained in the housing. The motor has a driveshaft. The motor has a first power input terminal and a second power input terminal. The trigger is coupled to the housing and is accessible external to the housing. The control circuit is mounted to the housing and is electrically coupled to the motor. The control circuit has a trigger switch circuit having a circuit trace arrangement and a movable contactor element. The circuit trace arrangement has a plurality of elongate electrical contact rows. The movable contactor element has a plurality of contactor prongs. The movable contactor element is mechanically connected to the trigger. The plurality of elongate electrical contact rows includes a first elongate electrical contact row having a first electrical contact strip that is connected to the chassis ground. The plurality of contactor prongs has a first electrical contactor prong positioned for sliding engagement with the first elongate electrical contact row. The trigger is configured to slidably move the first electrical contactor prong along the first electrical contact strip to physically move an electrical connection between the first electrical contactor prong of the movable contactor element and the chassis ground.

The invention, in another form, is directed to a biopsy system that includes an intraosseous device and a biopsy driver that may be in any of the forms and configurations set forth herein.

BRIEF DESCRIPTION OF DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplifications set out herein illustrate at least one embodiment of the invention, and such exemplifications are not to be construed as limiting the scope of the invention in any manner.

DESCRIPTION OF EMBODIMENTS

Figure 1:
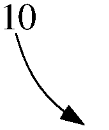
FIG. 1 is a perspective view of a biopsy system having a biopsy driver, an intraosseous device, and a coupler device having a proximal coupler portion and a distal coupler portion, with both coupler portions shown in respective latched positions, the biopsy driver being operable by a trigger.
Figure 1:
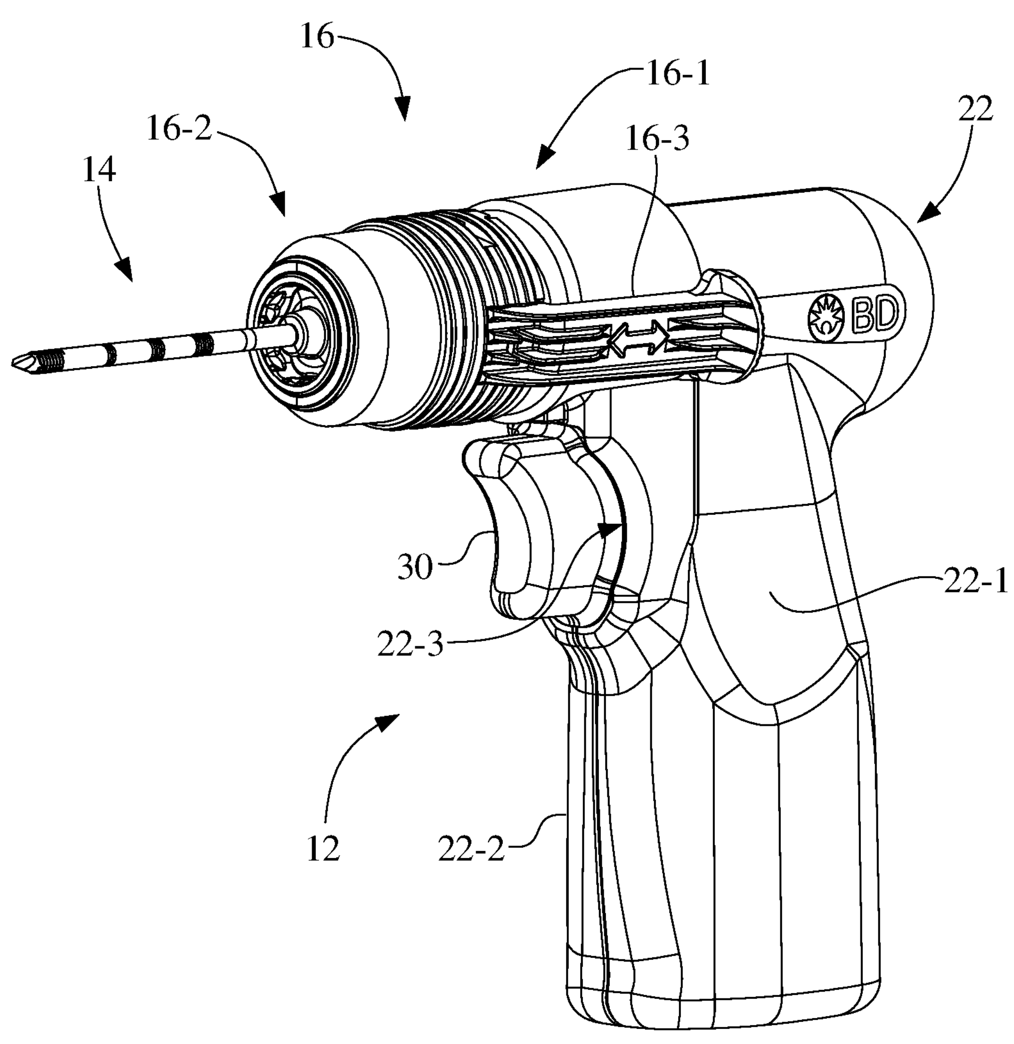

Referring to the drawings, and more particularly to FIG. 1, there is shown a biopsy system 10 in accordance with an embodiment of the present invention.

Figure 3:
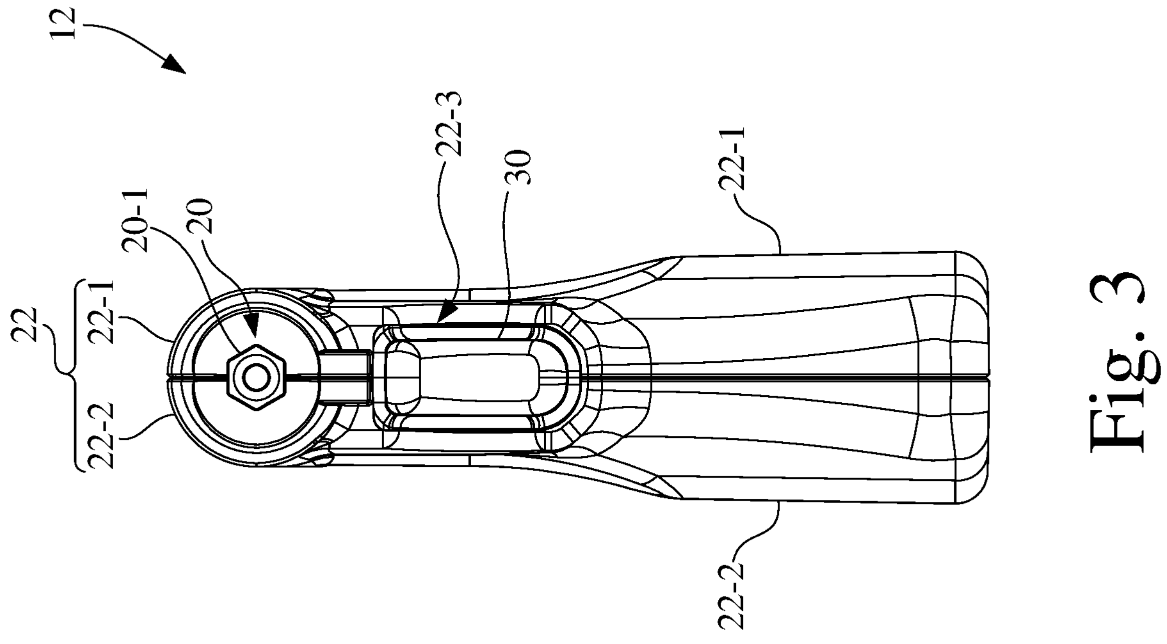
FIG. 3 is a front view of the biopsy driver of FIGS. 1 and 2.
Figure 2:
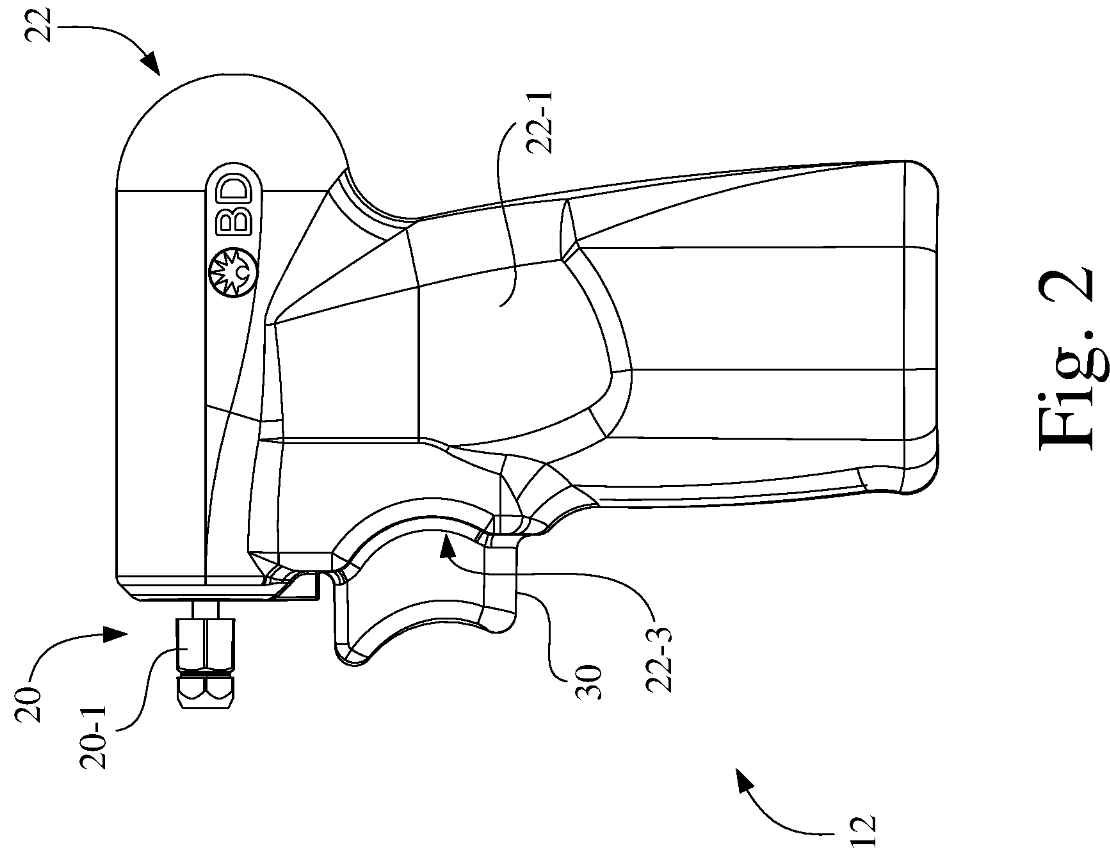
FIG. 2 is a side view of the biopsy driver of FIG. 1.
Figure 4:
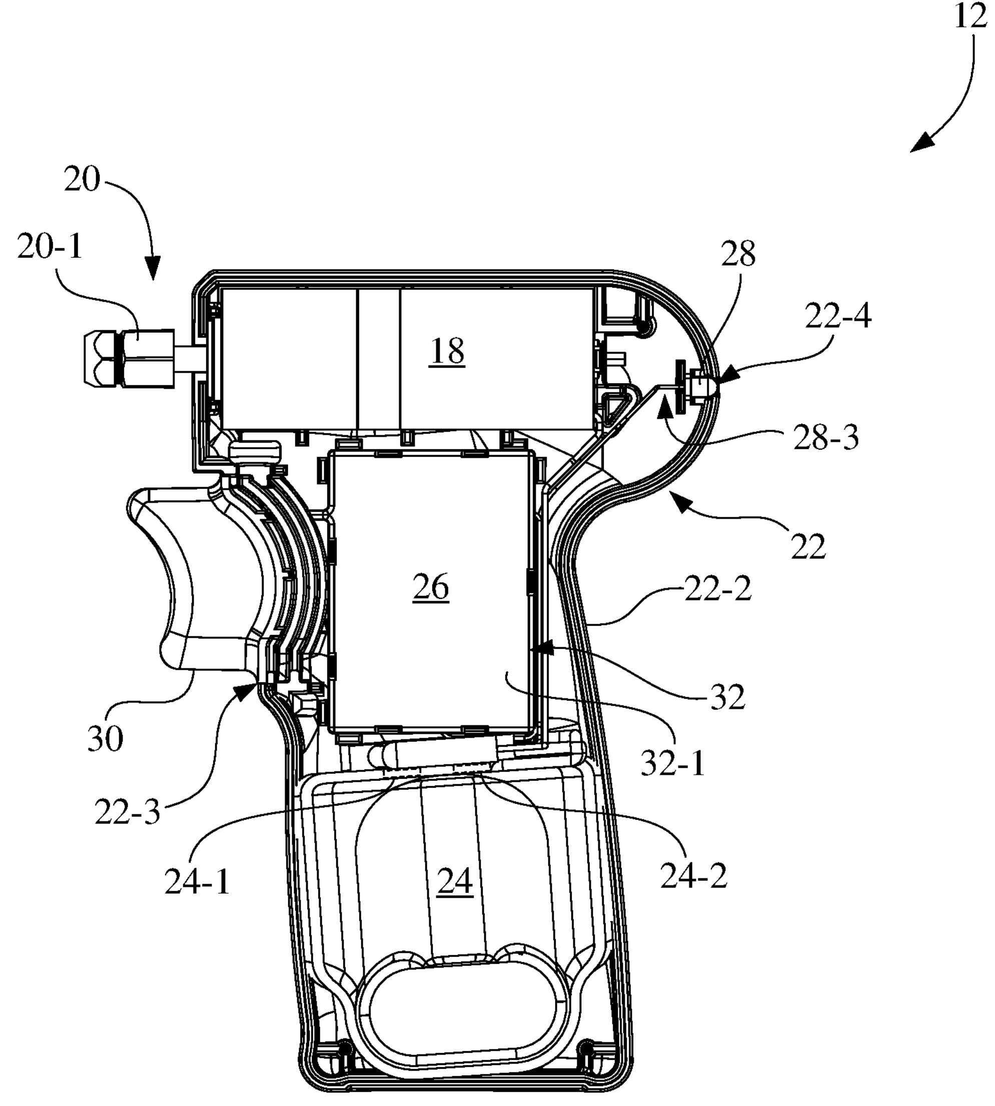
FIG. 4 is a side view of the biopsy driver of FIG. 2, with the left-half housing portion removed to expose a motor, a battery supply, a control module having a trigger, and a light emitting diode.

Biopsy system 10 includes a biopsy driver 12, an intraosseous device 14, and a coupler device 16. Referring also to FIGS. 2-4, in the present embodiment, biopsy driver 12 has a motor 18 having a driveshaft 20. In the configuration shown in FIG. 1, intraosseous device 14 is mechanically coupled to driveshaft 20 of biopsy driver 12 via coupler device 16, wherein intraosseous device 14 is rotationally driven by driveshaft 20 of biopsy driver 12. Motor 18 is, for example, a direct current (DC) motor.

In the present embodiment, driveshaft 20 of biopsy driver 12 is releasably connectable to a proximal coupler portion 16-1 of coupler device 16. Driveshaft 20 may have a polygonal arrangement of drive surfaces 20-1, wherein the polygonal arrangement may be, for example, hexagonal configured to engage corresponding driven features of the proximal coupler portion 16-1 of coupler device 16. Coupler device 16 has a distal coupler portion 16-2 that is releasably connectable to intraosseous device 14. Distal coupler portion 16-2 of coupler device 16 includes an external operator arm 16-3 that is longitudinally operable (e.g., push or pull) to release intraosseous device 14 to facilitate an exchange of intraosseous device 14, e.g., during a biopsy procedure. Intraosseous device 14 may be, for example, a biopsy needle assembly having a distal coupler portion configured to facilitate one or more of cutting, boring, and/or coring of bone tissue.

In an alternative embodiment, for example, intraosseous device 14 may be configured for direct connection to driveshaft 20 of biopsy driver 12.

Motor 18 may be, for example, a brushed motor having a permanent magnet stator. Motor 18 has a first power input terminal 18-1 (e.g., negative terminal) and a second power input terminal 18-2 (e.g., positive terminal). First power input terminal 18-1 and second power input terminal 18-2 are each connected to the brushes of motor 18. Motor 18, may be, for example, a Maxon® model DCX22S GB SL 12V motor having graphite commutation brushes, and having a planetary gearhead with a gear reduction of 44:1 at driveshaft 20, said motor being available from Maxon Precision Motors, Inc., Taunton, MA 02780 US. The graphite commutation brushes are electrically connected to first power input terminal 18-1 and second power input terminal 18-2.

Referring to FIGS. 1-3, biopsy driver 12 includes a housing 22. Housing may be made of an electrically insulative material, such as a non-conductive plastic. In the present embodiment, housing 22 is formed as a split case that includes a left-half housing portion 22-1 and a right-half housing portion 22-2.

In FIG. 4, left-half housing portion 22-1 is removed to expose the components contained in and/or mounted to housing 22. In addition to motor 18, housing 22 contains a battery supply 24, a control module 26, and a light emitting diode (LED) 28, with each of battery supply 24, control module 26, and light emitting diode (LED) 28 being mounted to housing 22. Control module 26 includes a trigger 30.

Housing 22 includes a distal opening 22-3 and a proximal aperture 22-4. Trigger 30 extends distally through distal opening 22-3 in housing 22 so as to be accessible to a user for operating biopsy driver 12. Stated differently, trigger 30 is slidably coupled to housing 22 and is accessible to the user external to housing 22. LED 28 is positioned at proximal aperture 22-4 of housing 22, wherein LED 28 is visible to a user of biopsy driver 12 through proximal aperture 22-4. LED 28 simultaneously provides to the user both a visual indication (e.g., by LED illumination brightness) of the rotational speed of driveshaft 20 of motor 18 and a visual indication (e.g., by a color change) of a present battery charge level of battery supply 24. LED 28 includes a green element 28-1 and a red element 28-2 (see FIG. 6).

Battery supply 24 is a DC power source having a supply voltage V+. In the present embodiment, battery supply 24 is a non-rechargeable and non-replaceable DC power source for use by biopsy driver 12. When the usable battery capacity of battery supply 24 is depleted, the user will dispose of the entirety of biopsy driver 12. However, in alternative embodiments, battery supply 24 may be replaced with a rechargeable and/or replaceable DC power source.

Battery supply 24 may be, for example, an 18-volt (V) DC battery pack having one or more batteries. In the present embodiment, for example, battery supply 24 may include six 3-volt model CR2 lithium batteries that are connected in series with an LR4-450F fuse so as to provide a nominal battery pack voltage of 18 V as an initial supply voltage V+. Battery supply 24 includes a positive terminal 24-1 and a negative terminal 24-2. Negative terminal 24-2 of battery supply 24 is selectively coupled to or decoupled from a chassis ground 44 by trigger switch circuit 54.

Battery supply 24 electrically interfaces with control module 26. Stated differently, battery supply 24 is electrically coupled to each of motor 18 and LED 28 via control module 26. The nominal battery capacity (full charge) of battery supply 24 may be, for example, approximately 850 mAh. The battery charge depletion from full charge, i.e., through use of biopsy driver 12, will be referred to herein as the present battery charge level of battery supply 24.

Figure 5:
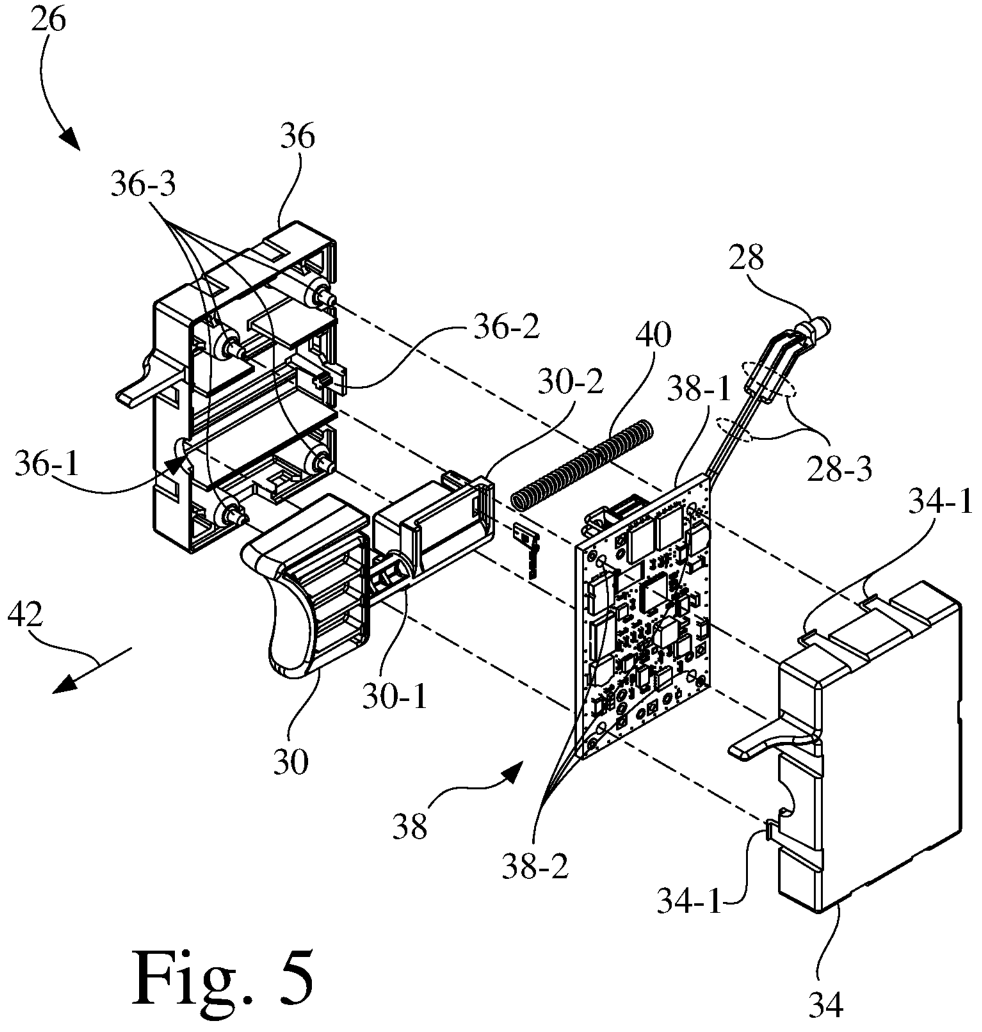
FIG. 5 is an exploded view of the control module of FIG. 4, which exposes a control circuit of the biopsy driver, the control circuit having a printed circuit board and a movable contactor element connected to the trigger.

Referring to FIGS. 4 and 5, control module 26 includes a case 32 having a left-half case portion 34 and a right-half case portion 36. Referring to FIG. 5, control module 26 includes a control circuit 38 contained in case 32. Control circuit 38 is mounted to housing 22 via case 32 and is electrically coupled to motor 18 (see also FIG. 6). Control circuit 38 includes a printed circuit board 38-1 to which the electronic components of control circuit 38 are mounted. LED 28 is electrically connected to printed circuit board 38-1 via LED leads 28-3. Printed circuit board 38-1 includes a plurality of mounting holes 38-2.

Right-half case portion 36 includes a trigger channel 36-1 that is sized and shaped to slidably carry trigger 30. More particularly, a slide portion 30-1 of trigger 30 slidably resides in trigger channel 36-1. A spring 40 is received in a proximal portion of trigger channel 36-1 and resides between a proximal end 30-2 of trigger 30 and a proximal wall 36-2 of trigger channel 36-1 to bias trigger 30 in a distal direction 42. Also, right-half case portion 36 includes a plurality of mounting posts 36-3 configured, e.g., in size, shape, and spacing, to engage corresponding mounting holes 38-2 of printed circuit board 38-1.

Left-half case portion 34 is connected to right-half case portion 36 via a plurality of snap-fit members 34-1 to enclose control circuit 38 and slide portion 30-1 of trigger 30, such that trigger 30 is slidably mounted to case 32 of control module 26.

Figure 6:
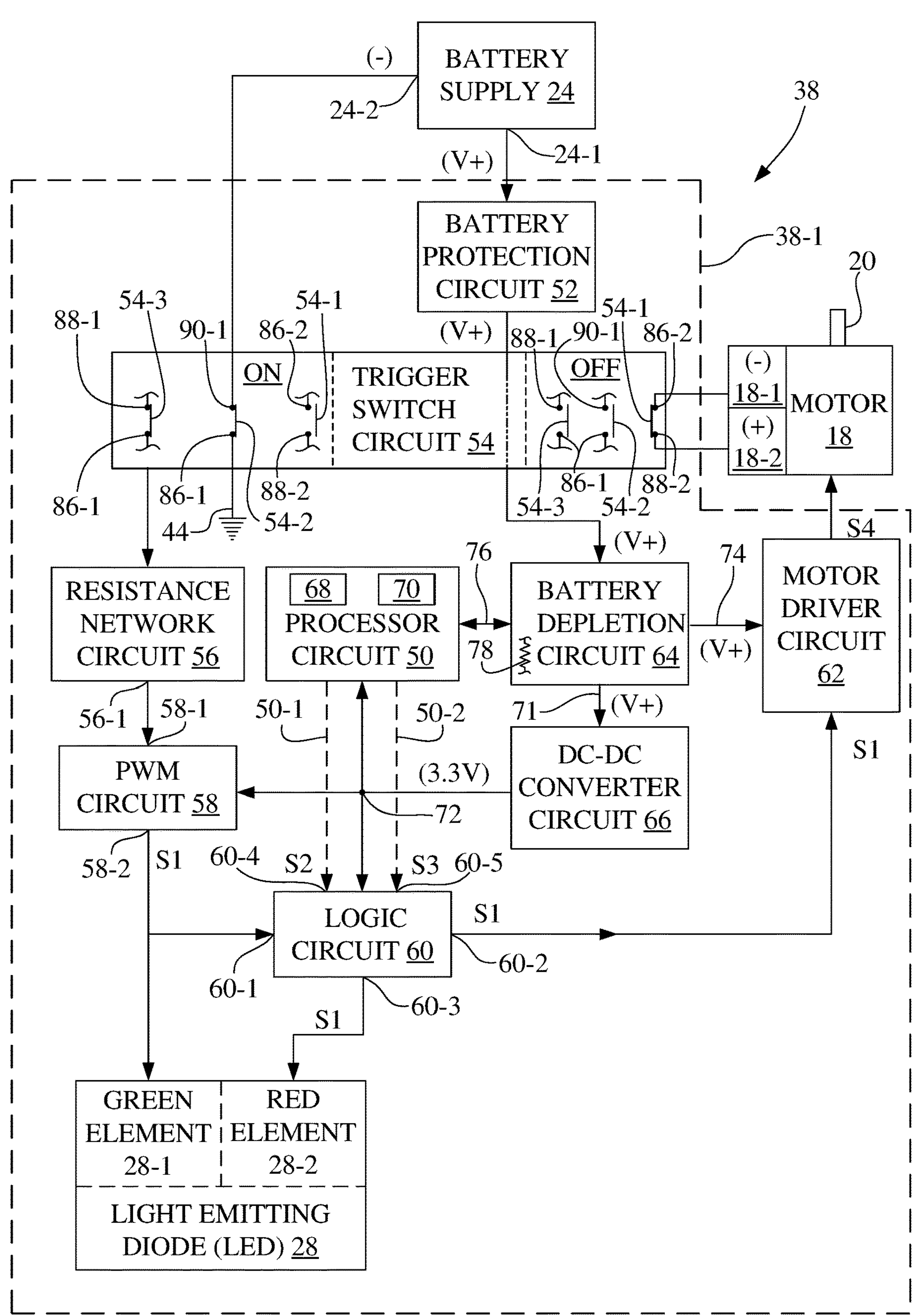
FIG. 6 is a block diagram of the control circuit of FIG. 5, which is shown coupled to the battery supply and the motor of FIG. 4.

FIG. 6 shows a block diagram of control circuit 38. In the present embodiment, control circuit 38 serves as an electrical interface between battery supply 24 and motor 18. Control circuit 38 includes a processor circuit 50, a battery protection circuit 52, a trigger switch circuit 54, a resistance network circuit 56, a pulse width modulation (PWM) circuit 58, a logic circuit 60, a motor driver circuit 62, a battery depletion circuit 64, a DC-DC converter circuit 66, and LED 28. Optionally, the components of controller circuit 38 may be formed as one or more application specific integrated circuits (ASIC).

Control circuit 38 is configured to control the operation of motor 18, to control a brightness of LED 28 dependent upon the duty cycle of the variable pulse width signal S1 of PWM circuit 58 to indicate a rotational speed of motor 18, and to control a color of LED 28 to indicate the present battery charge level of battery supply 24. In other words, the brightness of LED 28 increases in correspondence with an increase in rotational speed of motor 18, the brightness of LED 28 decreases in correspondence with a decrease in rotational speed of motor 18, and the color of LED 28 changes based on threshold events associated with the present battery charge level of battery supply 24.

Processor circuit 50 may be, for example, a microcontroller unit (MCU), such as an EFM8SB1, 8-bit MCU, available from Silicon Labs of Austin, Texas, US. Processor circuit 50 has a programmable microprocessor 68 and associated circuitry, such as an input/output interface, clock, buffers, etc., and a memory circuit 70. Microprocessor 68 may be, for example, 8051 core processor. Memory circuit 70 is communicatively coupled to processor circuit 50, e.g., via internal bus circuit traces, and is a non-transitory electronic memory. Memory circuit 70 may include both volatile electronic memory and non-volatile electronic memory. Such volatile electronic memory may be, for example, random access memory (RAM). Such non-volatile electronic memory may be, for example, read only memory (ROM), electronically erasable programmable ROM (EEPROM), flash memory, etc.

DC-DC converter circuit 66 is electrically coupled to battery depletion circuit 64 via a power bus 71, wherein battery depletion circuit 64 supplies the supply voltage V+ to DC-DC converter circuit 66. DC-DC converter circuit 66 may be in the form of an ASIC that is configured to convert, i.e., step down, the supply voltage V+ to a 3.3 volt supply voltage for use in providing electrical power via a power bus 72 to each of processor circuit 50, PWM circuit 58, and logic circuit 60.

Processor circuit 50 is communicatively coupled to logic circuit 60 via a communication link 50-1 and a communication link 50-2. Processor circuit 50 generates two control signals S2 and S3, each having an enable state and a disable state. In the present embodiment, processor circuit 50 generates a PWM output enable signal S2 (active high) and a battery depletion warning signal S3 (active high). Battery depletion warning signal S3 serves as a red element 28-2 enable signal.

Each of a low capacity threshold value, an end-of-life threshold value, and a remaining battery charge value is stored in memory circuit 70, e.g., in flash memory. The remaining battery charge value will be updated periodically by the present battery charge level of battery supply 24 as determined by processor circuit 50 and battery depletion circuit 64.

The low capacity threshold value may be, for example, a hexadecimal value that corresponds to a charge level designated to alerting the user of battery depletion. The low capacity threshold value may be, for example, 70 percent of the total initial charge on battery supply 24. For example, if the total initial capacity/charge on battery supply 24 is 850 milliamp-hours (mAh), or its equivalent, then the low capacity threshold value may be 255 mAh. Alternatively, these values may represent coulombs, i.e., ampere-seconds.

The end-of-life threshold value may be, for example, a hexadecimal value that corresponds to a charge level designated to end the operation of biopsy driver 12. The end-of-life threshold value may be used to ensure that biopsy driver 12 is not used beyond its intended life, e.g., in view of wear and/or material fatigue over time. The end-of-life threshold value may be, for example, 80 percent of the total initial charge on battery supply 24. For example, if the total initial charge on battery supply 24 is 850 mAh, then the end-of-life threshold value may be 170 mAh. Alternatively, these values may represent coulombs.

Processor circuit 50 is configured via software and/or firmware residing in memory circuit 70 to execute program instructions to perform functions associated with biopsy driver 12, such as for example, providing enable/disable signals to logic circuit 60 so as to selectively pass a variable pulse width signal S1 that controls a rotational speed of motor 18 and/or an illumination of red element 28-2 of LED 28, and monitoring the charge depletion of battery supply 24.

Battery protection circuit 52 is configured to ensure that the polarity of battery supply 24 is correct when connected to control circuit 38, e.g., at the time of manufacture. Biopsy driver 12 will not be operational until the proper polarity of battery supply 24 in relation to battery protection circuit 52 of control circuit 38 is achieved.

In the present embodiment, trigger switch circuit 54 is a multi-part sliding switch arrangement that defines three switching operations, depicted schematically in FIG. 6 as having a braking switch 54-1, a ground switch 54-2, and a resistance select switch 54-3. First power input terminal 18-1 and second power input terminal 18-2 of motor 18 are selectively coupled to each other or decoupled from each other by braking switch 54-1. Negative terminal 24-2 of battery supply 24 is selectively coupled to or decoupled from chassis ground 44 by ground switch 54-2. An output resistance of resistance network circuit 56 is selected based on a linear position of resistance select switch 54-3.

As depicted in FIG. 6, trigger switch circuit 54 has an OFF state and an ON state.

When trigger switch circuit 54 is in the OFF state, trigger switch circuit 54 is configured to disconnect negative terminal 24-2 of battery supply 24 from chassis ground 44 and to connect first power input terminal 18-1 of motor 18 to the second power input terminal 18-2 of motor 18 to facilitate a short-circuit braking of motor 18. In the OFF state, braking switch 54-1 is closed, and both of ground switch 54-2 and resistance select switch 54-3 is open.

When trigger switch circuit 54 is in the ON state, trigger switch circuit 54 is configured to connect negative terminal 24-2 of battery supply 24 to chassis ground 44 and to select a resistance value from resistance network circuit 56 to select a desired duty cycle of the variable pulse width signal S1 generated by PWM circuit 58. In the ON state, braking switch 54-1 is open, and both of ground switch 54-2 and resistance select switch 54-3 is closed. It is noted that trigger switch circuit 54 is configured such that braking switch 54-1 is open prior to the closing of either of ground switch 54-2 or resistance select switch 54-3, and that the timing of an initial closing of ground switch 54-2 and resistance select switch 54-3 may be staggered.

Trigger switch circuit 54 will be discussed in more detail later below.

Figure 8:
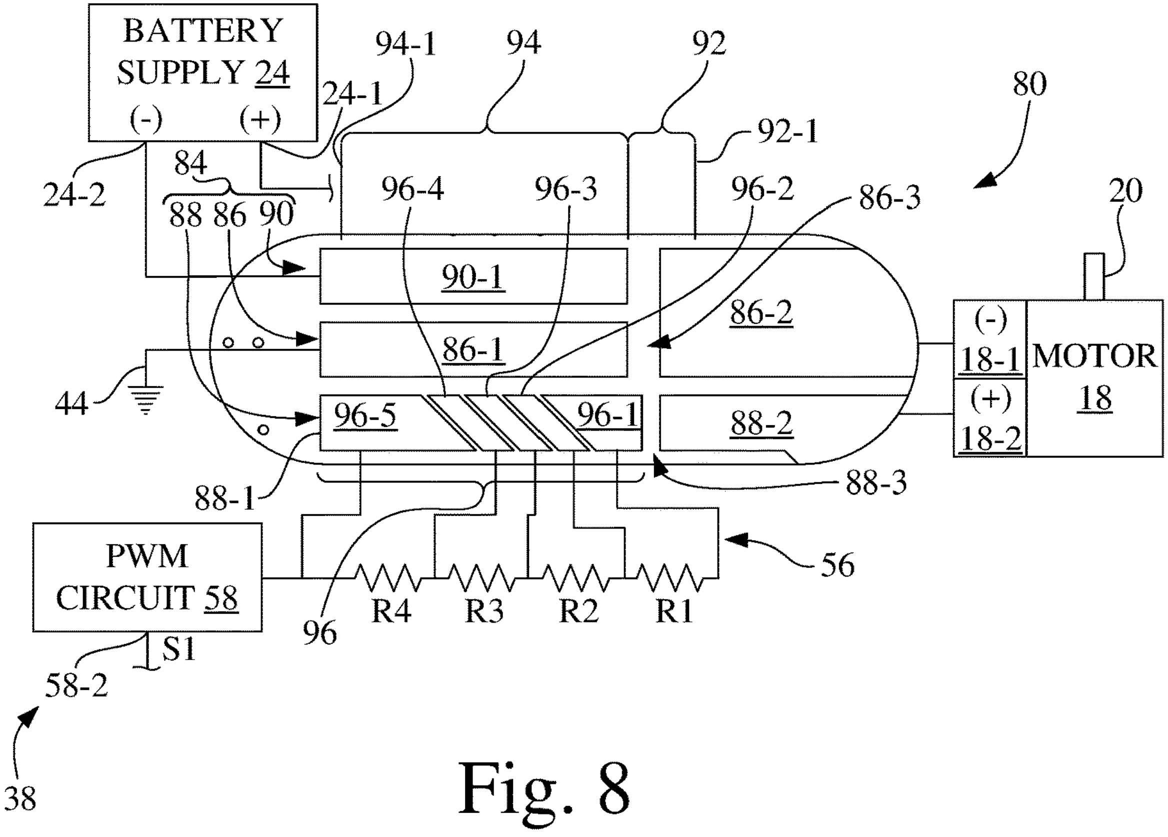
FIG. 8 is a partial schematic of the circuit trace arrangement portion of the printed circuit board in relation to the battery supply, the motor, and the resistor network circuit and PWM circuit of the control circuit.

Resistance network circuit 56 includes a plurality of resistors connected in series, such as the plurality of resistors R1, R2, R3, R4 shown in FIG. 8. The plurality of resistors connected in series define a plurality of sets of resistors. A resistance output 56-1 of resistance network circuit 56 is connected to an input 58-1 of PWM circuit 58. A resistance value selected from resistance network circuit 56 by resistance select switch 54-3 of trigger switch circuit 54 is used to select a desired duty cycle of a variable pulse width signal S1 generated by PWM circuit 58.

PWM circuit 58 is configured to generate a variable pulse width signal S1 to control a rotational speed of motor 18 based upon a duty cycle of the variable pulse width signal S1. PWM circuit 58 has an output 58-2 that is electrically coupled to green element 28-1 of LED 28 such that a brightness (i.e., light intensity) of green element 28-1 of LED 28 is dependent upon the duty cycle of the variable pulse width signal S1. Output 58-2 of PWM circuit 58 also is electrically coupled, via logic circuit 60, to each of the red element 28-2 of LED 28 and motor driver circuit 62, such that logic circuit 60 selectively and independently supplies (e.g., passes) variable pulse width signal S1 to each of the red element 28-2 of LED 28 and motor driver circuit 62. As such, PWM circuit 58 is communicatively coupled to each of green element 28-1 of LED 28 and red element 28-2 of LED 28.

The selection of resistance in resistance network circuit 56 results in a selection of the duty cycle of the variable pulse width signal S1 generated by PWM circuit 58. The variable pulse width signal S1 generated by PWM circuit 58 also is supplied to the green element 28-1 of LED 28, and to a logic input 60-1 of logic circuit 60.

Logic circuit 60 is electrically interposed between PWM circuit 58 and motor 18. Logic circuit 60 is configured, according to one aspect, to selectively pass the variable pulse width signal S1 to motor 18. Logic circuit 60 is configured, according to another aspect, to control illumination of the red element 28-2 of LED 28.

In the present embodiment, logic circuit 60 may be formed, for example, by two, two input AND gates. Logic circuit 60 has two outputs: PWM output 60-2 and logic output 60-3. One input of each of the two AND gates is electrically connected to logic input 60-1 of logic circuit 60. The other input of one of the two AND gates is electrically connected to logic input 60-4 of logic circuit 60, and other input of the other of the two AND gates is electrically connected to logic input 60-5 of logic circuit 60. Logic input 60-4 of logic circuit 60 is communicatively coupled to processor circuit 50 to receive PWM output enable signal S2 to turn on PWM output 60-2 so that logic circuit 60 passes variable pulse width signal S1 to motor driver circuit 62. Logic input 60-5 of logic circuit 60 is communicatively coupled to processor circuit 50 to receive a battery depletion warning signal S3 to selectively turn on logic output 60-3 so that logic circuit 60 passes variable pulse width signal S1 to red element 28-2 of LED 28.

Motor driver circuit 62 is electrically connected to battery depletion circuit 64 via power bus 74 so as to receive supply voltage V+ to power the electrical/electronic components of motor driver circuit 62. Motor driver circuit 62 includes power transistor components to convert the variable pulse width signal S1 generated by PWM circuit 58 to a motor speed control signal S4, e.g., having a pulse amplitude at the desired voltage level (e.g., V+) and having the same duty cycle as the variable pulse width signal S1. Motor driver circuit 62 may also include motor protection circuitry, as is known in the art. In one embodiment, for example, motor driver circuit 62 may include a half H-Bridge gate driver to control two MOSFET components to generate motor speed control signal S4 according to the variable pulse width signal S1 generated by PWM circuit 58 and passed by logic circuit 60. The half H-Bridge gate driver will enable or disable each MOSFET component as required to achieve motor speed control signal S4, which will correspond to the variable pulse width signal S1 generated by PWM circuit 58.

Battery depletion circuit 64 is configured to determine a present battery charge level of battery supply 24. Battery depletion circuit 64 may be, for example, an ASIC that provides a current measurement input to processor circuit 50. Battery depletion circuit 64 is communicatively coupled to processor circuit 50 via bidirectional communication link 76. Bidirectional communication link 76 may be formed, for example, by electrical interface circuitry and circuit traces on printed circuit board 38-1.

Battery depletion circuit 64 includes a sense resistor 78 (e.g., 2.0 ohms) that is connected in series with positive terminal 24-1 of battery supply 24. The current through sense resistor 78 is measured over time to determine a calculated reduction of the battery capacity of battery supply 24. Battery depletion circuit 64 provides to processor circuit 50 a real-time readout of sensed current measurements from which processor circuit 50 calculates a present battery charge level of battery supply 24 that is stored in memory circuit 70. Battery depletion circuit 64 is communicatively coupled to red element 28-2 of LED 28 by way of processor circuit 50 and logic circuit 60.

Processor circuit 50 is configured to execute program instructions to sample the sense resistor 78 over time to calculate the present battery charge level of battery supply 24, e.g., in milliamp-hours (mAh). Processor circuit 50 further executes program instructions to update the remaining battery charge value stored in memory circuit 70 with the present battery charge level. Stated differently, the present battery charge level of battery supply 24 may be used to continually periodically update the remaining battery charge value stored in memory circuit 70.

Processor circuit 50 is configured to execute program instructions to generate and send a control signal, in the form of a PWM output enable signal S2, to logic circuit 60, wherein PWM output enable signal S2 has an enable state to enable a PWM output 60-2 of logic circuit 60 and has a disable state to disable PWM output 60-2 of logic circuit 60. Processor circuit 50 is configured to execute program instructions to generate the enable state of PWM output enable signal S2 when the remaining battery charge value is greater than the end-of-life threshold value so that logic circuit 60 enables PWM output 60-2 of logic circuit 60, so that logic circuit 60 passes the variable pulse width signal S1 to motor 18 via motor driver circuit 62. Also, processor circuit 50 is configured to execute program instructions to generate the disable state of PWM output enable signal S2 when the remaining battery charge value is equal to or less than the end-of-life threshold value so that logic circuit 60 disables PWM output 60-2 of logic circuit 60 so that logic circuit 60 does not pass the variable pulse width signal S1 to motor 18, which in effect disables motor 18.

In one embodiment, for example, a power cycle to supply electrical power to motor 18 is initiated by actuation of the trigger 30. Processor circuit 50 is configured so as to, at the beginning of each power cycle, execute program instructions to implement a logic sequence of not passing a variable pulse width signal to the motor when the remaining battery charge value is equal to or less than the end-of-life threshold value. Thus, a present power cycle may be completed without interruption regardless of the battery charge level; however, a subsequent power cycle will be prohibited when the remaining battery charge value is equal to or less than the end-of-life threshold value. Stated differently, processor circuit 50 is configured such that a present power cycle is completed without interruption regardless of the battery charge level, but a subsequent power cycle is prohibited when the remaining battery charge value is equal to or less than the end-of-life threshold value.

Processor circuit 50 further executes program instructions to generate a control signal, in the form of a battery depletion warning signal S3, having an enable state and a disable state, wherein battery depletion warning signal S3 is in the enable state when the remaining battery charge value is equal to or less than (below) the low capacity threshold so as to enable illumination of red element 28-2 of LED 28 by the variable pulse width signal S1 generated by PWM circuit 58, wherein the brightness of the illumination of red element 28-2 of LED 28 is dependent upon the duty cycle of the variable pulse width signal S1.

Figure 7:
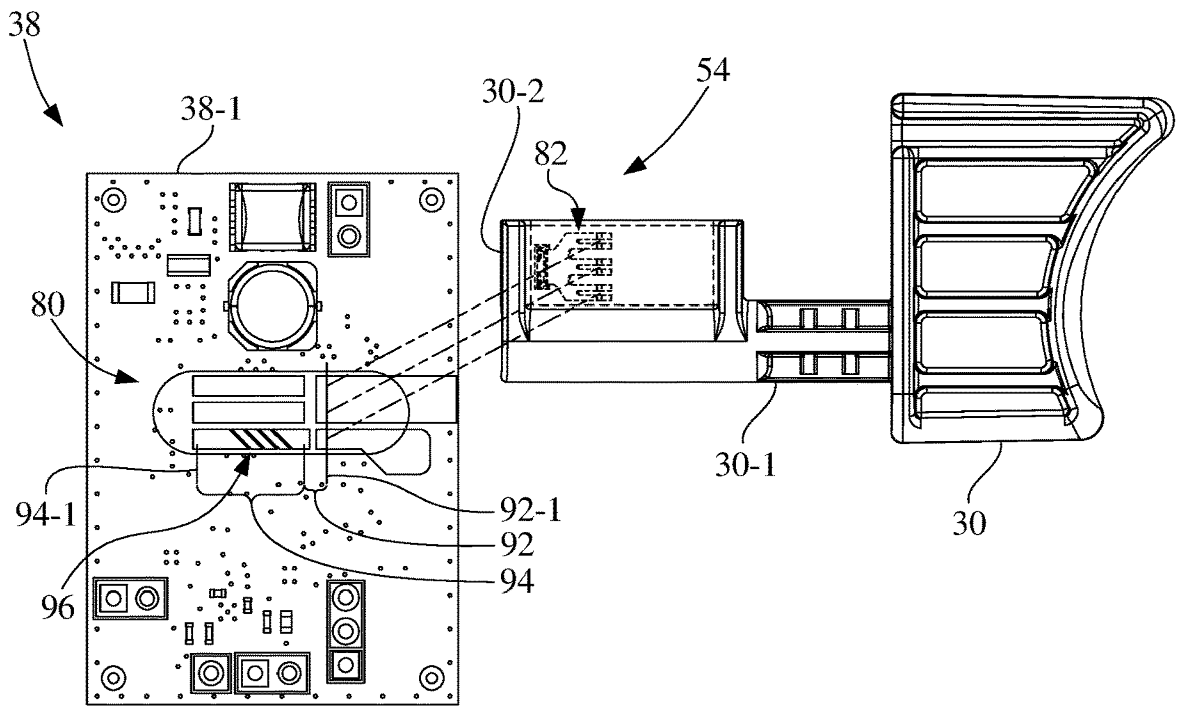
FIG. 7 is an enlarged side view of an opposite side of the printed circuit board, the movable contactor element, and the trigger shown in FIG. 5, wherein a trigger circuit is formed by a circuit trace arrangement of the printed circuit board and the movable contactor element connected to the trigger, and wherein the trigger and the movable contactor element are projected away from the printed circuit board for clarity.
Figure 9:
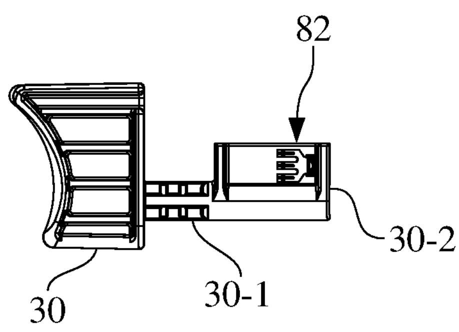
FIG. 9 is a side view of the movable contactor element mechanically connected to the trigger, corresponding to the orientation shown in FIG. 5, and opposite to the orientation shown in FIG. 7.

Referring to FIG. 7, there is shown an opposite side of printed circuit board 38-1 and trigger 30 of control circuit 38 to that shown in FIG. 5, wherein trigger 30 is projected away from printed circuit board 38-1 for clarity. Trigger switch circuit 54 of control circuit 38 includes a circuit trace arrangement 80 and a movable contactor element 82 (see also FIGS. 9 and 10). Each of circuit trace arrangement 80 and movable contactor element 82 is made of an electrically conductive metal. Trigger 30 may be made of an electrically insulative material, such as a non-conductive plastic. Referring to FIGS. 7 and 9, movable contactor element 82 is mechanically connected to trigger 30.

Referring to FIGS. 7 and 8, circuit trace arrangement 80 of trigger switch circuit 54 has a plurality of elongate electrical contact rows 84. Plurality of elongate electrical contact rows 84 include a first elongate electrical contact row 86, a second elongate electrical contact row 88, and a third elongate electrical contact row 90. First elongate electrical contact row 86 is positioned as the center trace in circuit trace arrangement 80 so as to define a middle ground between second elongate electrical contact row 88 and third elongate electrical contact row 90. Second elongate electrical contact row 88 is laterally spaced and electrically separated (i.e., insulated) from first elongate electrical contact row 86. Likewise, third elongate electrical contact row 90 is laterally spaced and electrically separated (i.e., insulated) from first elongate electrical contact row 86.

Figure 10:
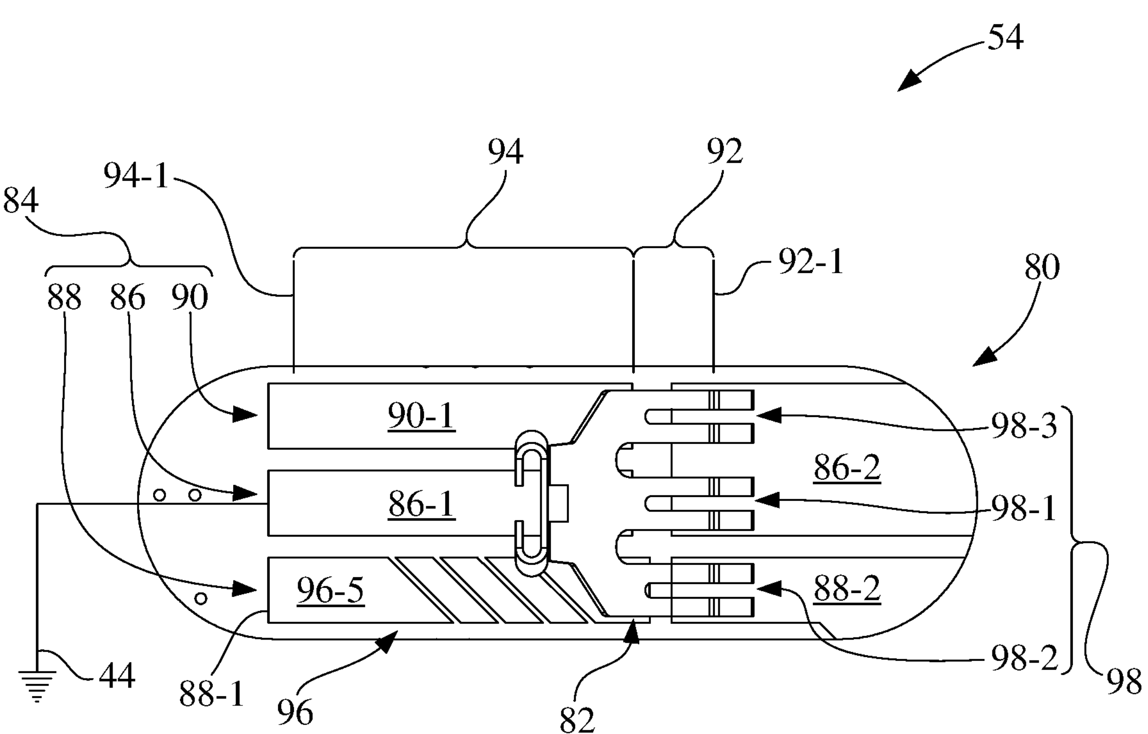
FIG. 10 is an enlarged side view of the trigger circuit of FIG. 7, wherein the movable contactor element is in the home position of an OFF range of positions.
Figure 11:
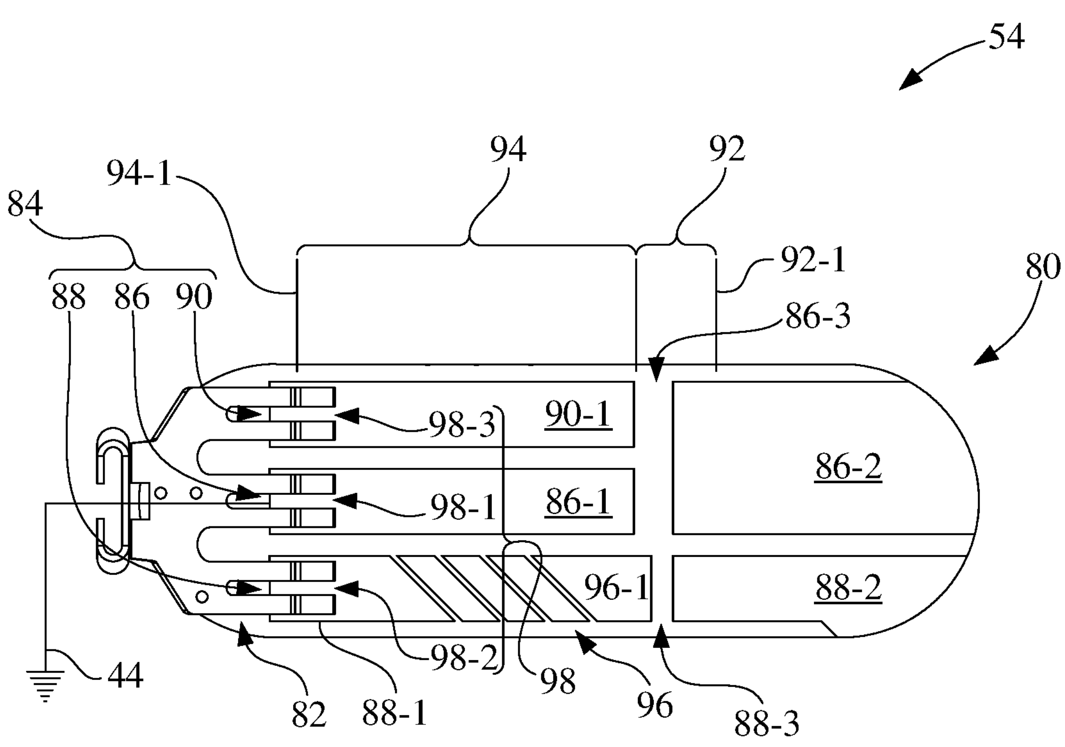
FIG. 11 is an enlarged side view of the trigger circuit of FIG. 7, wherein the movable contactor element is positioned in the maximum motor rotational speed position of an ON range of positions.

Referring also to FIGS. 10 and 11, defined perpendicular to first elongate electrical contact row 86, second elongate electrical contact row 88, and third elongate electrical contact row 90 of circuit trace arrangement 80 is an OFF range of positions 92 and an ON range of positions 94 of trigger switch circuit 54. The OFF range of positions 92 includes a home position 92-1, wherein home position 92-1 is an OFF position corresponding to when trigger 30 and movable contactor element 82 are fully distally biased by spring 40 (see FIG. 5). FIG. 10 shows movable contactor element 82 in the home position 92-1 of the OFF range of positions 92. Referring to FIG. 11 in conjunction with FIGS. 1, 5, and 7, by depressing (e.g., pulling) trigger 30, movable contactor element 82 is moved to transition from the OFF range of positions 92 into the ON range of positions 94. FIG. 11 shows movable contactor element 82 in a maximum motor rotational speed position 94-1 of the ON range of positions 94, i.e., trigger 30 having been fully pulled by the user of biopsy driver 12.

Anywhere within the OFF range of positions 92 of trigger switch circuit 54, a longitudinal position of movable contactor element 82 relative to circuit trace arrangement 80 results in a disconnection of chassis ground 44 from negative terminal 24-2 of battery supply 24, and as such, no electrical power is available to motor 18. Also, when movable contactor element 82 is at home position 92-1 of the OFF range of positions 92, movable contactor element 82 facilitates an electrically short of first power input terminal 18-1 of motor 18 to second power input terminal 18-2 of motor 18 so as to facilitate a short-circuit (dynamic) braking of motor 18. The OFF range of positions 92 is provided to ensure that first power input terminal 18-1 of motor 18 is no longer short-circuited to second power input terminal 18-2 of motor 18 prior to establishing electrical power to motor 18 in the ON range of positions 94 of trigger switch circuit 54.

Anywhere within the ON range of positions 94, a longitudinal position of movable contactor element 82 relative to circuit trace arrangement 80 selectively and movably connects chassis ground 44 to negative terminal 24-2 of battery supply 24, such that electrical power is available to motor 18. Also referring to FIG. 8, anywhere within the ON range of positions 94, a longitudinal position of movable contactor element 82 relative to circuit trace arrangement 80 selectively connects chassis ground 44 to one set of a plurality of sets of resistors set (R1, R2, R3, R4); set (R2, R3, R4); set (R3, R4); set (R4); and set (no R) of the plurality of series connected resistors R1, R2, R3, R4 of resistance network circuit 56, so as to select a resistance value to in turn select the desired duty cycle of the variable pulse width signal S1 generated by PWM circuit 58, wherein variable pulse width signal S1 is used to select the rotational speed of motor 18.

Referring again to FIG. 8, first elongate electrical contact row 86 has a first electrical contact strip 86-1 and a first electrical contact pad 86-2. First electrical contact pad 86-2 is longitudinally spaced from and electrically separated (i.e., insulated) from first electrical contact strip 86-1 to define a first gap 86-3. First electrical contact strip 86-1 is connected to chassis ground 44. First electrical contact pad 86-2 is electrically connected to first power input terminal 18-1 (e.g., negative terminal) of motor 18.

Second elongate electrical contact row 88 has a second electrical contact strip 88-1 and a second electrical contact pad 88-2. Second electrical contact pad 88-2 is longitudinally spaced from and electrically separated (i.e., insulated) from second electrical contact strip 88-1 to define a second gap 88-3. Second electrical contact strip 88-1 has a plurality of longitudinally spaced and electrically separated (i.e., insulated) electrical contact segments 96 configured to facilitate a selection of a rotational speed of motor 18. In the present embodiment, the plurality of electrical contact segments 96 includes segment 96-1, segment 96-2, segment 96-3, segment 96-4, and segment 96-5. Second electrical contact pad 88-2 is electrically connected to second power input terminal 18-2 (e.g., positive terminal) of motor 18.

Resistance network circuit 56 is formed by the plurality of series connected resistors R1, R2, R3, R4. Each of resistors R1, R2, R3, R4 may be, for example, 4.7k ohms. Each resistor of the plurality of series connected resistors R1, R2, R3, R4 bridges the insulated gap between adjacent pairs of the plurality of electrical contact segments 96. Stated differently, the plurality of series connected resistors R1, R2, R3, R4 define a plurality of sets of resistors, namely: set (R1, R2, R3, R4); set (R2, R3, R4); set (R3, R4); set (R4); and set (no R), with each set of resistors being associated with one segment of the plurality of electrical contact segments 96. Set (no R) means a set void of any of resistors R1, R2, R3, R4. For example, a selection of segment 96-1 will select resistor set (R1, R2, R3, R4); selection of segment 96-3 will select resistor set (R3, R4); and, selection of segment 96-5 will select resistor set (no R). The selected resistor set proves a resistance value to PWM circuit 58 for generation of the variable pulse width signal S1, which is used to select the rotational speed of motor 18.

Third elongate electrical contact row 90 has a third electrical contact strip 90-1 that is longitudinally spaced from and electrically separated (i.e., insulated) from a portion of first electrical contact pad 86-2. Also, third electrical contact strip 90-1 is laterally spaced from and electrically separated (insulated) from first electrical contact strip 86-1. Third electrical contact strip 90-1 is connected to negative terminal 24-2 of battery supply 24.

Referring to FIGS. 7 and 9-12, movable contactor element 82 is a unitary metal structure having a plurality of contactor prongs 98 that cantilever outwardly from a body 100. In the present embodiment, the plurality of contactor prongs 98 include a first electrical contactor prong 98-1, a second electrical contactor prong 98-2, and a third electrical contactor prong 98-3. Second electrical contactor prong 98-2 is laterally spaced from first electrical contactor prong 98-1, and third electrical contactor prong 98-3 is laterally spaced from first electrical contactor prong 98-1, wherein first electrical contactor prong 98-1, second electrical contactor prong 98-2, and the third electrical contactor prong 98-3 are permanently electrically connected together. In the present embodiment, each of first electrical contactor prong 98-1, second electrical contactor prong 98-2, and third electrical contactor prong 98-3 is configured as a split fork to provide a pair of contactor surfaces.

Referring to FIGS. 10 and 11, first electrical contactor prong 98-1 of movable contactor element 82 is aligned for electrical engagement with and movement along first elongate electrical contact row 86. Second electrical contactor prong 98-2 of movable contactor element 82 is aligned for electrical engagement with and movement along second elongate electrical contact row 88. Third electrical contactor prong 98-3 of movable contactor element 82 is aligned for electrical engagement with and movement along third elongate electrical contact row 90.

Figure 12:
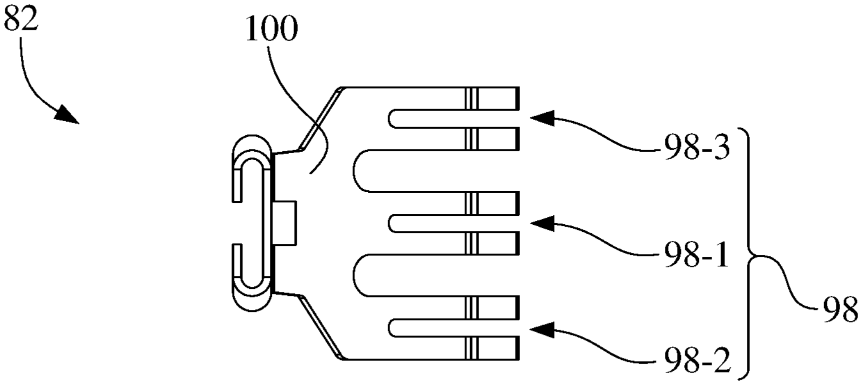
FIG. 12 is an enlarged side view of the movable contactor element of FIGS. 7 and 9-11.

Referring to FIGS. 10-12 in relation to FIGS. 7-9, first electrical contactor prong 98-1 is positioned for sliding engagement with first elongate electrical contact row 86. Trigger 30 is configured to slidably move first electrical contactor prong 98-1 along first electrical contact strip 86-1 to physically move an electrical connection between first electrical contactor prong 98-1 of movable contactor element 82 and chassis ground 44.

Referring to 7-10, when trigger 30 and movable contactor element 82 are in the OFF range of positions 92, negative terminal 24-2 of battery supply 24 is not coupled to chassis ground 44 and no electrical power is supplied to control circuit 38. In the present embodiment, when trigger 30 and movable contactor element 82 are in the home position 92-1 of the OFF range of positions 92 (see FIG. 10), first electrical contactor prong 98-1 is electrically engaged with first electrical contact pad 86-2 and second electrical contactor prong 98-2 is electrically engaged with second electrical contact pad 88-2 so as to, with reference to FIG. 8, electrically short first power input terminal 18-1 of motor 18 to second power input terminal 18-2 of motor 18 to facilitate a short-circuit braking of motor 18.

Referring to FIGS. 7-9 and 11, when trigger 30 and movable contactor element 82 are in the ON range of positions 94, negative terminal 24-2 of battery supply 24 is coupled to chassis ground 44 and electrical power is supplied to control circuit 38. With regard to trigger switch circuit 54, in the present embodiment, when trigger 30 and movable contactor element 82 are in the ON range of positions 94, first electrical contactor prong 98-1 is electrically engaged with first electrical contact strip 86-1 and second electrical contactor prong 98-2 is electrically engaged with a particular segment of the plurality of longitudinally spaced and electrically separated electrical contact segments 96 to select the desired duty cycle of the variable pulse width signal S1 generated by PWM circuit 58 to select the rotational speed of motor 18. Also, when trigger 30 and movable contactor element 82 are in the ON range of positions 94, first electrical contactor prong 98-1 is electrically engaged with first electrical contact strip 86-1 and the third electrical contactor prong 98-3 is electrically engaged with third electrical contact strip 90-1 so as to, with reference to FIG. 8, connect negative terminal 24-2 of battery supply 24 to chassis ground 44 to facilitate supplying electrical power to control circuit 38 through battery depletion circuit 64 (see also FIG. 6).

Referring to FIGS. 8, 10 and 11, a spacing (gap 86-3) between first electrical contact strip 86-1 and first electrical contact pad 86-2 of first elongate electrical contact row 86 is greater than a spacing (gap 88-3) between second electrical contact strip 88-1 and second electrical contact pad 88-2 of second elongate electrical contact row 88. When trigger 30 and movable contactor element 82 are in the home position 92-1 of the OFF range of positions 92 (see FIG. 10), first electrical contactor prong 98-1 is electrically engaged with first electrical contact pad 86-2 and second electrical contactor prong 98-2 is electrically engaged with second electrical contact pad 88-2 so as to electrically short first power input terminal 18-1 of motor 18 to second power input terminal 18-2 of motor 18 to facilitate a short-circuit braking of motor 18.

When trigger 30 and movable contactor element 82 is moved out of the OFF range of positions 92 toward the ON range of positions 94, second electrical contactor prong 98-2 of movable contactor element 82 electrically engages a first segment 96-1 of second electrical contact strip 88-1 of second elongate electrical contact row 88 prior to when first electrical contactor prong 98-1 of movable contactor element 82 electrically engages first electrical contact strip 86-1 of first elongate electrical contact row 86 and prior to when the third electrical contactor prong 98-3 of movable contactor element 82 electrically engages third electrical contact strip 90-1 of first elongate electrical contact row 86, so as to ensure that a selection of the rotational speed of motor 18 via resistance network circuit 56 is made prior to connecting battery supply 24 to chassis ground 44 (see FIG. 8) for supplying electrical power to control circuit 38 (see also FIG. 6).

The following items also relate to the invention:

In one embodiment, the invention relates to a biopsy driver. The biopsy driver may include a housing. A battery supply may be contained in the housing. The battery supply may have a positive terminal and a negative terminal. The negative terminal may (be configured to) be selectively coupled to or(/and) decoupled from a chassis ground. A motor may be contained in the housing. The motor may have a driveshaft. The motor may have a first power input terminal and a second power input terminal. A trigger may be coupled to the housing and is accessible external to the housing. A control circuit may be mounted to the housing and may be electrically coupled to the motor. The control circuit may have a trigger switch circuit, a resistance network circuit, and a pulse width modulation circuit. The trigger switch circuit may have an OFF state and an ON state. The resistance network circuit may be coupled to an input of the pulse width modulation circuit. The pulse width modulation circuit may be configured to generate a variable pulse width signal to control a rotational speed of the motor. The biopsy driver may be configured such that when the trigger switch circuit is in the ON state, the trigger switch circuit may be configured to connect the negative terminal of the battery supply to the chassis ground and may be configured to select a resistance value from the resistance network circuit to select a desired duty cycle of the variable pulse width signal generated by the pulse width modulation circuit.

In the embodiment according to the immediately preceding paragraph, when the trigger switch circuit is in the OFF state, the trigger switch circuit may be configured to: disconnect the negative terminal of the battery supply from the chassis ground and to connect the first power input terminal of the motor and to the second power input terminal of the motor to facilitate a short-circuit braking of the motor.

In some embodiments, the control circuit may comprise a light emitting diode (LED) that may have a first color element and a second color element. The first color element is visually distinguishable from the second color element. A battery depletion circuit may be configured to determine a present battery charge level of the battery source. The battery depletion circuit may be communicatively coupled to the second color element of the LED. The pulse width modulation circuit may be electrically coupled to each of the first color element of the LED and the second color element of the LED. The control circuit may be configured to control a brightness of the LED dependent upon the duty cycle of the variable pulse width signal to indicate a rotational speed of the motor and may be configured to control a color of the LED to indicate the present battery charge level of the battery supply.

In the embodiment according to the immediately preceding paragraph, the control circuit may comprise a processor circuit that may have a microprocessor circuit and a memory circuit, and may have a low capacity threshold value and a remaining battery charge value stored in the memory circuit. The battery depletion circuit may be communicatively coupled to the processor circuit. The battery depletion circuit may have a sense resistor connected in series with the positive terminal of the battery supply. The processor circuit may be configured to: execute program instructions to sample the sense resistor over time to calculate a present battery charge level of the battery source, execute program instructions to update the remaining battery charge value stored in the memory circuit with the present battery charge level, and, execute program instructions to generate a battery depletion warning signal that may have an enable state and a disable state, wherein the battery depletion warning signal is in the enable state when the remaining battery charge value is equal to or less than the low capacity threshold so as to enable illumination of the second color element of the LED by the variable pulse width signal, wherein the brightness of the illumination of the second color element of the LED is dependent upon the duty cycle of the variable pulse width signal.

In the embodiment according to the immediately preceding paragraph, a logic circuit may be interposed between the pulse width modulation circuit and the motor. The logic circuit may be configured to selectively pass the variable pulse width signal to the motor. The processor circuit may be communicatively coupled to the logic circuit. The control circuit may have an end-of-life threshold value stored in the memory circuit. The processor circuit may be configured to execute program instructions to send a control signal to the logic circuit. The control signal may have an enable state to enable a PWM output of the logic circuit and may have a disable state to disable the PWM output of the logic circuit. The processor circuit may be configured to execute program instructions to generate the enable state of the control signal when the remaining battery charge value is greater than the end-of-life threshold value so that the logic circuit enables the PWM output of the logic circuit so that the logic circuit passes the variable pulse width signal to the motor. The processor circuit may be configured to execute program instructions to generate the disable state of the control signal when the remaining battery charge value is equal to or less than the end-of-life threshold value so that the logic circuit disables the PWM output of the logic circuit so that the logic circuit does not pass the variable pulse width signal to the motor to effect a disabling of the motor.

In any of the embodiments, the resistance network circuit may include a plurality of resistors connected in series. The plurality of resistors connected in series may define a plurality of sets of resistors. The trigger switch circuit may include a circuit trace arrangement and a movable contactor element, wherein a longitudinal position of the movable contactor element relative to the circuit trace arrangement selectively connects the chassis ground to one set of the plurality of sets of resistors of the plurality of resistors connected in series to select the resistance value to select the desired duty cycle of the variable pulse width signal generated by the pulse width modulation circuit to select the rotational speed of the motor.

In the embodiment according to the immediately preceding paragraph, the circuit trace arrangement may have a plurality of elongate electrical contact rows. The plurality of elongate electrical contact rows may include a first elongate electrical contact row that may have a first electrical contact strip that is connected to the chassis ground. The movable contactor element may have a plurality of contactor prongs. The movable contactor element may be mechanically connected to the trigger. The plurality of contactor prongs may have a first electrical contactor prong positioned for sliding engagement with the first elongate electrical contact row. The trigger may be configured to slidably move the first electrical contactor prong along the first electrical contact strip to physically and slidably move an electrical connection of the first electrical contactor prong of the movable contactor element with the chassis ground.

In the embodiment according to the immediately preceding paragraph, the trigger and the movable contactor element may have an OFF range of positions associated with the OFF state (i.e. a range of positions associated with the OFF state) and may have an ON range of positions associated with the ON state (i.e. a range of positions associated with the ON state). The biopsy driver may be configured such that when the trigger and the movable contactor element are in the OFF range of positions, the negative terminal of the battery supply is not coupled to the chassis ground and no electrical power is supplied to the control circuit. The biopsy driver may be configured such that when the trigger and the movable contactor element are in the ON range of positions, the negative terminal of the battery supply is coupled to the chassis ground and electrical power is supplied to the control circuit.

In the embodiment according to the immediately preceding paragraph, the plurality of contactor prongs of the movable contactor element may include a second electrical contactor prong laterally spaced from the first electrical contactor prong. The second electrical contactor prong may be permanently electrically connected to the first electrical contactor prong. The plurality of elongate electrical contact rows may include a second elongate electrical contact row laterally spaced from the first elongate electrical contact row, wherein the second electrical contactor prong of the movable contactor element is aligned for electrical engagement with and movement along the second elongate electrical contact row. The second elongate electrical contact row may have a second electrical contact strip that may have a plurality of longitudinally spaced and electrically separated electrical contact segments configured to facilitate a selection of the rotational speed of the motor. The biopsy driver may be configured such that when the trigger and the movable contactor element are in the ON range of positions, the second electrical contactor prong is electrically engaged with a particular segment of the plurality of longitudinally spaced and electrically separated electrical contact segments to select the desired duty cycle of the variable pulse width signal generated by the pulse width modulation circuit to select the rotational speed of the motor.

In the embodiment according to the immediately preceding paragraph, the plurality of elongate electrical contact rows of the control circuit may include a third elongate electrical contact row that may have a third electrical contact strip laterally spaced from the first electrical contact strip. The third electrical contact strip may be connected to the negative terminal of the battery supply. The plurality of contactor prongs of the movable contactor element may include a third electrical contactor prong electrically connected with each of the first electrical contactor prong and the second electrical contactor prong. The third electrical contactor prong may be aligned for electrical engagement with and movement along the third elongate electrical contact row. The biopsy driver may be configured such that when the trigger and the movable contactor element are in the ON range of positions, the third electrical contactor prong is electrically engaged with the third electrical contact strip to connect the negative terminal of the battery supply to the chassis ground to facilitate supplying electrical power to the control circuit.

In the embodiment according to either of the two immediately preceding paragraphs, the first elongate electrical contact row may have a first electrical contact pad that is longitudinally spaced from and electrically separated from the first electrical contact strip to define a first gap. The first electrical contact pad may be electrically connected to the first power input terminal of the motor. The second elongate electrical contact row may have a second electrical contact pad that is longitudinally spaced from and electrically separated from the second electrical contact strip to define a second gap. The second electrical contact pad may be electrically connected to the second power input terminal of the motor. The biopsy driver may be configured such that when the trigger and the movable contactor element are in the OFF range of positions, the first electrical contactor prong is electrically engaged with the first electrical contact pad and the second electrical contactor prong is electrically engaged with the second electrical contact pad so as to electrically short the first power input terminal of the motor to the second power input terminal of the motor to facilitate a short-circuit braking of the motor.

In the embodiment according to the immediately preceding paragraph, the trigger switch circuit (and the biopsy driver) may be configured such that the third electrical contact strip of the third elongate electrical contact row is longitudinally spaced from (and electrically separated from) a portion of the first electrical contact pad by the first gap. The first gap may be greater than the second gap. The biopsy driver may be configured such that when the trigger and the movable contactor element are moved out of the OFF range of positions toward the ON position, the second electrical contactor prong of the movable contactor element electrically engages a first segment of the second electrical contact strip of the second elongate electrical contact row prior to when the first electrical contactor prong of the movable contactor element electrically engages the first electrical contact strip of the first elongate electrical contact row and the third electrical contactor prong of the movable contactor element electrically engages the third electrical contact strip of the first elongate electrical contact row, so as to ensure that a selection of the rotational speed of the motor is made prior to supplying electrical power to the control circuit.

In another embodiment, the invention relates to a biopsy system comprising an intraosseous device and the biopsy driver according to any of preceding paragraphs. The intraosseous device may be (configured to be) mechanically coupled to the driveshaft of the motor.

In another embodiment, the invention relates to a biopsy driver comprising a housing. A battery supply may be contained in the housing. The battery supply may have a positive terminal and a negative terminal. The negative terminal may (be configured to) be selectively coupled to a chassis ground. A motor may be contained in the housing. The motor may have a driveshaft. The motor may have a first power input terminal and a second power input terminal. A trigger may be coupled to the housing and is accessible external to the housing. A control circuit may be mounted to the housing and may be electrically coupled to the motor. The control circuit may have a trigger switch circuit that may have a circuit trace arrangement and a movable contactor element. The circuit trace arrangement may have a plurality of elongate electrical contact rows. The movable contactor element may have a plurality of contactor prongs. The movable contactor element may be mechanically connected to the trigger. The plurality of elongate electrical contact rows may include a first elongate electrical contact row that may have a first electrical contact strip that is connected to the chassis ground. The plurality of contactor prongs may have a first electrical contactor prong positioned for sliding engagement with the first elongate electrical contact row. The trigger may be configured to slidably move the first electrical contactor prong along the first electrical contact strip to physically move an electrical connection between the first electrical contactor prong of the movable contactor element and the chassis ground.

In the embodiment according to the immediately preceding paragraph, the trigger and the movable contactor element may have an OFF range of positions (i.e. a range of positions associated with the OFF state) and may have an ON range of positions (i.e. a range of positions associated with the ON state). The biopsy driver may be configured such that when the trigger and the movable contactor element are in the OFF range of positions, the negative terminal of the battery supply is not coupled to the chassis ground and no electrical power is supplied to the control circuit. The biopsy driver may be configured such that when the trigger and the movable contactor element are in the ON range of positions, the negative terminal of the battery supply is coupled to the chassis ground and electrical power is supplied to the control circuit.

In the embodiment according to the immediately preceding paragraph, the plurality of contactor prongs of the movable contactor element includes a second electrical contactor prong laterally spaced from the first electrical contactor prong. The second electrical contactor prong may be permanently electrically connected to the first electrical contactor prong. The plurality of elongate electrical contact rows may include a second elongate electrical contact row laterally spaced from the first elongate electrical contact row. The second electrical contactor prong of the movable contactor element may be aligned for electrical engagement with and movement along the second elongate electrical contact row. The second elongate electrical contact row may have a second electrical contact strip that may have a plurality of longitudinally spaced and electrically separated electrical contact segments configured to facilitate selection of a rotational speed of the motor. The biopsy driver may be configured such that when the trigger and the movable contactor element are in the ON range of positions, the second electrical contactor prong is electrically engaged with a particular segment of the plurality of longitudinally spaced electrical contact segments to select the rotational speed of the motor.

In the embodiment according to the immediately preceding paragraph, the control circuit may comprise a battery depletion circuit configured to determine a present battery charge level of the battery source. The plurality of elongate electrical contact rows of the control circuit may include a third elongate electrical contact row that may have a third electrical contact strip laterally spaced from the first electrical contact strip. The plurality of contactor prongs of the movable contactor element may include a third electrical contactor prong electrically connected with each of the first electrical contactor prong and the second electrical contactor prong. The third electrical contactor prong may be aligned for electrical engagement with and movement along the third elongate electrical contact row. The biopsy driver may be configured such that when the trigger and the movable contactor element are in the ON range of positions, the third electrical contactor prong is electrically engaged with the third electrical contact strip to connect the negative terminal of the battery supply to the chassis ground to facilitate supplying electrical power to the battery depletion circuit.

In the embodiment according to the immediately preceding paragraph, the control circuit comprises a light emitting diode (LED) that may have a green element and a red element. The battery depletion circuit may be communicatively coupled to the red element of the LED. The pulse width modulation circuit may be electrically coupled to each of the green element of the LED and the red element of the LED. The control circuit (and the biopsy driver) may be configured to control a brightness of the LED dependent upon a duty cycle of variable pulse width signal to indicate a rotational speed of the motor and may be configured to control a color of the LED to indicate the present battery charge level of the battery supply.

In the embodiment according to the immediately preceding paragraph, the control circuit may comprise a processor circuit that may have a microprocessor circuit and memory circuit, and may have a low capacity threshold value and a remaining battery charge value stored in the memory circuit. The battery depletion circuit may include a sense resistor connected in series with the positive terminal of the battery supply. The processor circuit may be configured to execute program instructions to sample the sense resistor over time to calculate a present battery charge level of the battery source, and to update the remaining battery charge value stored in the memory circuit of the processor circuit. The processor circuit may be configured to execute program instructions to supply a battery depletion warning signal to the red element of the light emitting diode when the remaining battery charge value is equal to or less than the low capacity threshold value.

In the embodiment according to the immediately preceding paragraph, the control circuit may include an end-of-life threshold value stored in the memory circuit of the processor circuit. The processor circuit may be configured to execute program instructions to not pass a variable pulse width signal to the motor when the remaining battery charge value is equal to or less than the end-of-life threshold value.

In the embodiments according to any of the immediately preceding five paragraphs, the first elongate electrical contact row may have a first electrical contact pad that is longitudinally spaced from and electrically separated from the first electrical contact strip. The first electrical contact pad may be electrically connected to the first power input terminal of the motor. The second elongate electrical contact row may have a second electrical contact pad that is longitudinally spaced from and electrically separated from the second electrical contact strip. The second electrical contact pad may be electrically connected to the second power input terminal of the motor. The biopsy driver may be configured such that when the trigger and the movable contactor element are in the OFF range of positions, the first electrical contactor prong is electrically engaged with the first electrical contact pad and the second electrical contactor prong is electrically engaged with the second electrical contact pad so as to electrically short the first power input terminal of the motor to the second power input terminal of the motor to facilitate a short-circuit braking of the motor.

In the embodiment according to the immediately preceding paragraph, the third electrical contact strip of the third elongate electrical contact row may be longitudinally spaced from (and electrically separated from) a portion of the first electrical contact pad.

In the embodiment according to either of the two immediately preceding paragraphs, a spacing between the first electrical contact strip and the first electrical contact pad of the first elongate electrical contact row may be greater than the spacing between the second electrical contact strip and the second electrical contact pad of the second elongate electrical contact row.

In some embodiments, a power cycle to supply electrical power to the motor may be initiated by actuation of the trigger. The control circuit includes a processor circuit that may have a microprocessor circuit and memory circuit, and may have a remaining battery charge value stored in the memory circuit. A battery depletion circuit may be configured to determine a present battery charge level of the battery source. An end-of-life threshold value may be stored in the memory circuit of the processor circuit. The processor circuit may be configured such that a present power cycle is completed without interruption regardless of the battery charge level, but a subsequent power cycle is prohibited when the remaining battery charge value is equal to or less than the end-of-life threshold value.

In another embodiment, the invention relates to a biopsy system that comprises an intraosseous device and the biopsy driver according to any of the immediately preceding eleven paragraphs. The intraosseous device may be (configured to be) mechanically coupled to the driveshaft of the motor.

As used herein, the term "coupled", and its derivatives, is an electrical coupling and/or mechanical coupling, intended to embrace any operationally functional connection, i.e., a direct connection (e.g., no intervening components) or an indirect connection (e.g., having intervening components). The term "selectively coupled" means a selection between coupled and decoupled, e.g., wherein the coupling or decoupling occurs through a switch component. The term "communicatively coupled" means an electrical coupling that may be used to carry data and/or a switchable voltage level.

Words of degree, such as approximately, are relative modifiers intended to indicate permissible variation from the characteristic so modified. Such terms are not intended to be limited to the absolute value of the characteristic which it modifies, but rather possessing more of the physical or functional characteristic than the opposite, and approaching or approximating such a physical or functional characteristic.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

The invention claimed is:

1. A biopsy driver, comprising:

a housing;

a battery supply contained in the housing, the battery supply having a positive terminal and a negative terminal, the negative terminal being selectively coupled to or decoupled from a chassis ground;

a motor contained in the housing, the motor having a driveshaft, the motor having a first power input terminal and a second power input terminal;

a trigger coupled to the housing and accessible external to the housing; and a control circuit mounted to the housing and electrically coupled to the motor, the control circuit having a trigger switch circuit, a resistance network circuit, and a pulse width modulation circuit, the trigger switch circuit having an OFF state and an ON state, the resistance network circuit being coupled to an input of the pulse width modulation circuit, the pulse width modulation circuit configured to generate a variable pulse width signal to control a rotational speed of the motor, wherein when the trigger switch circuit is in the ON state, the trigger switch circuit is configured to:

connect the negative terminal of the battery supply to the chassis ground to supply power to the control circuit such that both a ground switch and a resistance select switch are closed, and disconnect the first power input terminal of the motor from the second power input terminal of the motor such that a braking switch is open; and when the resistance select switch is closed, select a resistance value from the resistance network circuit to select a desired duty cycle of the variable pulse width signal generated by the pulse width modulation circuit.

2. The biopsy driver according to claim 1, wherein when the trigger switch circuit is in the OFF state, the trigger switch circuit is configured to:

disconnect the negative terminal of the battery supply from the chassis ground when the ground switch and the resistance select switch are open and power is not supplied to the control circuit; and connect the first power input terminal of the motor to the second power input terminal of the motor such that the braking switch is closed to facilitate a short-circuit braking of the motor.

3. The biopsy driver according to claim 1, wherein the control circuit comprises:

a light emitting diode (LED) having a first color element and a second color element, the first color element being visually distinguishable from the second color element;

a battery depletion circuit configured to determine a present battery charge level of the battery supply, the battery depletion circuit being communicatively coupled to the second color element of the LED; and the pulse width modulation circuit electrically coupled to each of the first color element of the LED and the second color element of the LED, wherein the control circuit is configured to control a brightness of the LED dependent upon the duty cycle of the variable pulse width signal to indicate a rotational speed of the motor and to control a color of the LED to indicate the present battery charge level of the battery supply.

4. The biopsy driver according to claim 3, wherein the control circuit further comprises:

a processor circuit having a microprocessor circuit and a memory circuit, and having a low capacity threshold value and a remaining battery charge value stored in the memory circuit; and the battery depletion circuit communicatively coupled to the processor circuit, the battery depletion circuit having a sense resistor connected in series with the positive terminal of the battery supply, the processor circuit configured to:

execute program instructions to sample the sense resistor over time to calculate a present battery charge level of the battery source, execute program instructions to update the remaining battery charge value stored in the memory circuit with the present battery charge level, and, execute program instructions to generate a battery depletion warning signal having an enable state and a disable state, wherein the battery depletion warning signal is in the enable state when the remaining battery charge value is equal to or less than the low capacity threshold so as to enable illumination of the second color element of the LED by the variable pulse width signal, wherein the brightness of the illumination of the second color element of the LED is dependent upon the duty cycle of the variable pulse width signal.

5. The biopsy driver according to claim 4, comprising:

a logic circuit interposed between the pulse width modulation circuit and the motor, the logic circuit configured to selectively pass the variable pulse width signal to the motor, and the processor circuit communicatively coupled to the logic circuit, and the control circuit having an end-of-life threshold value stored in the memory circuit, the processor circuit configured to execute program instructions to send a control signal to the logic circuit, the control signal having an enable state to enable a PWM output of the logic circuit and having a disable state to disable the PWM output of the logic circuit, the processor circuit configured to execute program instructions to generate the enable state of the control signal when the remaining battery charge value is greater than the end-of-life threshold value so that the logic circuit enables the PWM output of the logic circuit so that the logic circuit passes the variable pulse width signal to the motor, and the processor circuit configured to execute program instructions to generate the disable state of the control signal when the remaining battery charge value is equal to or less than the end-of-life threshold value so that the logic circuit disables the PWM output of the logic circuit so that the logic circuit does not pass the variable pulse width signal to the motor to effect a disabling of the motor.

6. The biopsy driver according to claim 1, comprising:

the resistance network circuit including a plurality of resistors connected in series, the plurality of resistors connected in series defining a plurality of sets of resistors, and the trigger switch circuit including a circuit trace arrangement and a movable contactor element, wherein a longitudinal position of the movable contactor element relative to the circuit trace arrangement selectively connects the chassis ground to one set of the plurality of sets of resistors of the plurality of resistors connected in series to select the resistance value to select the desired duty cycle of the variable pulse width signal generated by the pulse width modulation circuit to select the rotational speed of the motor.

7. The biopsy driver accordingly to claim 6, wherein:

the circuit trace arrangement has a plurality of elongate electrical contact rows, the plurality of elongate electrical contact rows including a first elongate electrical contact row having a first electrical contact strip that is connected to the chassis ground, the movable contactor element having a plurality of contactor prongs, the movable contactor element being mechanically connected to the trigger, the plurality of contactor prongs having a first electrical contactor prong positioned for sliding engagement with the first elongate electrical contact row, the trigger configured to slidably move the first electrical contactor prong along the first electrical contact strip to physically and slidably move an electrical connection of the first electrical contactor prong of the movable contactor element with the chassis ground.

8. The biopsy driver according to claim 7, wherein the trigger and the movable contactor element have an OFF range of positions associated with the OFF state and an ON range of positions associated with the ON state, the biopsy driver configured such that:

when the trigger and the movable contactor element are in the OFF range of positions, the negative terminal of the battery supply is not coupled to the chassis ground and no electrical power is supplied to the control circuit; and when the trigger and the movable contactor element are in the ON range of positions, the negative terminal of the battery supply is coupled to the chassis ground and electrical power is supplied to the control circuit.

9. The biopsy driver according to claim 8, wherein:

the plurality of contactor prongs of the movable contactor element includes a second electrical contactor prong laterally spaced from the first electrical contactor prong, the second electrical contactor prong being permanently electrically connected to the first electrical contactor prong;

the plurality of elongate electrical contact rows includes a second elongate electrical contact row laterally spaced from the first elongate electrical contact row, wherein the second electrical contactor prong of the movable contactor element is aligned for electrical engagement with and movement along the second elongate electrical contact row; and the second elongate electrical contact row having a second electrical contact strip having a plurality of longitudinally spaced and electrically separated electrical contact segments configured to facilitate a selection of the rotational speed of the motor, the biopsy driver configured such that when the trigger and the movable contactor element are in the ON range of positions, the second electrical contactor prong is electrically engaged with a particular segment of the plurality of longitudinally spaced and electrically separated electrical contact segments to select the desired duty cycle of the variable pulse width signal generated by the pulse width modulation circuit to select the rotational speed of the motor.

10. The biopsy driver according to claim 9, comprising:

the plurality of elongate electrical contact rows of the control circuit including a third elongate electrical contact row having a third electrical contact strip laterally spaced from the first electrical contact strip, the third electrical contact strip being connected to the negative terminal of the battery supply; and the plurality of contactor prongs of the movable contactor element including a third electrical contactor prong electrically connected with each of the first electrical contactor prong and the second electrical contactor prong, the third electrical contactor prong being aligned for electrical engagement with and movement along the third elongate electrical contact row, the biopsy driver configured such that when the trigger and the movable contactor element are in the ON range of positions, the third electrical contactor prong is electrically engaged with the third electrical contact strip to connect the negative terminal of the battery supply to the chassis ground to facilitate supplying electrical power to the control circuit.

11. The biopsy driver according to claim 9, comprising:

the first elongate electrical contact row having a first electrical contact pad that is longitudinally spaced from and electrically separated from the first electrical contact strip to define a first gap, the first electrical contact pad being electrically connected to the first power input terminal of the motor; and the second elongate electrical contact row having a second electrical contact pad that is longitudinally spaced from and electrically separated from the second electrical contact strip to define a second gap, the second electrical contact pad being electrically connected to the second power input terminal of the motor, the biopsy driver configured such that when the trigger and the movable contactor element are in the OFF range of positions, the first electrical contactor prong is electrically engaged with the first electrical contact pad and the second electrical contactor prong is electrically engaged with the second electrical contact pad so as to electrically short the first power input terminal of the motor to the second power input terminal of the motor to facilitate a short-circuit braking of the motor.

12. The biopsy driver according to claim 10, the trigger switch circuit configured such that:

the third electrical contact strip of the third elongate electrical contact row is longitudinally spaced from and electrically separated from a portion of the first electrical contact pad by the first gap;

the first gap is greater than the second gap; and when the trigger and the movable contactor element are moved out of the OFF range of positions toward the ON position, the second electrical contactor prong of the movable contactor element electrically engages a first segment of the second electrical contact strip of the second elongate electrical contact row prior to when the first electrical contactor prong of the movable contactor element electrically engages the first electrical contact strip of the first elongate electrical contact row and the third electrical contactor prong of the movable contactor element electrically engages the third electrical contact strip of the first elongate electrical contact row, so as to ensure that a selection of the rotational speed of the motor is made prior to supplying electrical power to the control circuit.

13. A biopsy system, comprising:

an intraosseous device; and the biopsy driver according to claim 1, the intraosseous device being mechanically coupled to the driveshaft of the motor.

14. A biopsy driver, comprising:

a housing;

a battery supply contained in the housing, the battery supply having a positive terminal and a negative terminal, the negative terminal being selectively coupled to a chassis ground;

a motor contained in the housing, the motor having a driveshaft, the motor having a first power input terminal and a second power input terminal;

a trigger coupled to the housing and accessible external to the housing; and a control circuit mounted to the housing and electrically coupled to the motor, the control circuit having a trigger switch circuit having a circuit trace arrangement and a movable contactor element, the circuit trace arrangement having a plurality of elongate electrical contact rows, the movable contactor element having a plurality of contactor prongs, the movable contactor element being mechanically connected to the trigger, the trigger and the movable contactor element have an OFF range of positions and an ON range of positions, the plurality of elongate electrical contact rows including a first elongate electrical contact row having a first electrical contact strip that is connected to the chassis ground, the plurality of contactor prongs having a first electrical contactor prong positioned for sliding engagement with the first elongate electrical contact row, the trigger configured to slidably move the first electrical contactor prong from the OFF range of positions spaced from the first electrical contact strip and the chassis ground to the ON range of positions coupled to the first electrical contact strip and the chassis ground along the first electrical contact strip to physically move an electrical connection between the first electrical contactor prong of the movable contactor element and the chassis ground.

15. The biopsy driver according to claim 14, the biopsy driver configured such that:

when the trigger and the movable contactor element are in the OFF range of positions, the negative terminal of the battery supply is not coupled to the chassis ground and no electrical power is supplied to the control circuit; and when the trigger and the movable contactor element are in the ON range of positions, the negative terminal of the battery supply is coupled to the chassis ground and electrical power is supplied to the control circuit.

16. The biopsy driver according to claim 15, wherein:

the plurality of contactor prongs of the movable contactor element includes a second electrical contactor prong laterally spaced from the first electrical contactor prong, the second electrical contactor prong being permanently electrically connected to the first electrical contactor prong;

the plurality of elongate electrical contact rows includes a second elongate electrical contact row laterally spaced from the first elongate electrical contact row, the second electrical contactor prong of the movable contactor element being aligned for electrical engagement with and movement along the second elongate electrical contact row; and the second elongate electrical contact row having a second electrical contact strip having a plurality of longitudinally spaced and electrically separated electrical contact segments configured to facilitate selection of a rotational speed of the motor, and the biopsy driver configured such that when the trigger and the movable contactor element are in the ON range of positions, the second electrical contactor prong is electrically engaged with a particular segment of the plurality of longitudinally spaced electrical contact segments to select the rotational speed of the motor.

17. The biopsy driver according to claim 16, wherein:

the control circuit comprises a battery depletion circuit configured to determine a present battery charge level of the battery supply;

the plurality of elongate electrical contact rows of the control circuit includes a third elongate electrical contact row having a third electrical contact strip laterally spaced from the first electrical contact strip; and the plurality of contactor prongs of the movable contactor element include a third electrical contactor prong electrically connected with each of the first electrical contactor prong and the second electrical contactor prong, the third electrical contactor prong being aligned for electrical engagement with and movement along the third elongate electrical contact row, the biopsy driver configured such that when the trigger and the movable contactor element are in the ON range of positions, the third electrical contactor prong is electrically engaged with the third electrical contact strip to connect the negative terminal of the battery supply to the chassis ground to facilitate supplying electrical power to the battery depletion circuit.

18. The biopsy driver according to claim 17, wherein the control circuit comprises:

a light emitting diode (LED) having a green element and a red element;

the battery depletion circuit communicatively coupled to the red element of the LED; and a pulse width modulation circuit electrically coupled to each of the green element of the LED and the red element of the LED, wherein:

the control circuit is configured to control a brightness of the LED dependent upon a duty cycle of variable pulse width signal to indicate a rotational speed of the motor and to control a color of the LED to indicate the present battery charge level of the battery supply.

19. The biopsy driver according to claim 18, wherein the control circuit comprises:

a processor circuit having a microprocessor circuit and memory circuit, and having a low capacity threshold value and a remaining battery charge value stored in the memory circuit; and the battery depletion circuit includes a sense resistor connected in series with the positive terminal of the battery supply, the processor circuit configured to execute program instructions to sample the sense resistor over time to calculate a present battery charge level of the battery supply, and to update the remaining battery charge value stored in the memory circuit of the processor circuit;

the processor circuit configured to execute program instructions to supply a battery depletion warning signal to the red element of the light emitting diode when the remaining battery charge value is equal to or less than the low capacity threshold value.

20. The biopsy driver according to claim 19, wherein the control circuit includes an end-of-life threshold value stored in the memory circuit of the processor circuit, the processor circuit configured to execute program instructions to not pass a variable pulse width signal to the motor when the remaining battery charge value is equal to or less than the end-of-life threshold value.

21. The biopsy driver according to claim 16, comprising:

the first elongate electrical contact row having a first electrical contact pad that is longitudinally spaced from and electrically separated from the first electrical contact strip, the first electrical contact pad being electrically connected to the first power input terminal of the motor; and the second elongate electrical contact row having a second electrical contact pad that is longitudinally spaced from and electrically separated from the second electrical contact strip, the second electrical contact pad being electrically connected to the second power input terminal of the motor, the biopsy driver configured such that when the trigger and the movable contactor element are in the OFF range of positions, the first electrical contactor prong is electrically engaged with the first electrical contact pad and the second electrical contactor prong is electrically engaged with the second electrical contact pad so as to electrically short the first power input terminal of the motor to the second power input terminal of the motor to facilitate a short-circuit braking of the motor.

22. The biopsy driver according to claim 17, wherein the third electrical contact strip of the third elongate electrical contact row is longitudinally spaced from and electrically separated from a portion of the first electrical contact pad.

23. The biopsy driver according to claim 21, wherein a spacing between the first electrical contact strip and the first electrical contact pad of the first elongate electrical contact row is greater than the spacing between the second electrical contact strip and the second electrical contact pad of the second elongate electrical contact row.

24. The biopsy driver according to claim 14, wherein a power cycle to supply electrical power to the motor is initiated by actuation of the trigger, wherein the control circuit includes:

a processor circuit having a microprocessor circuit and memory circuit, and having a remaining battery charge value stored in the memory circuit;

a battery depletion circuit configured to determine a present battery charge level of the battery supply;

an end-of-life threshold value stored in the memory circuit of the processor circuit; and the processor circuit configured such that a present power cycle is completed without interruption regardless of the battery charge level, but a subsequent power cycle is prohibited when the remaining battery charge value is equal to or less than the end-of-life threshold value.

25. A biopsy system, comprising:

an intraosseous device; and the biopsy driver according to claim 14, the intraosseous device being mechanically coupled to the driveshaft of the motor.

* * * * *